US006562967B2

(12) United States Patent
Deng et al.

(10) Patent No.: US 6,562,967 B2
(45) Date of Patent: *May 13, 2003

(54) KINETIC RESOLUTIONS OF CHIRAL 2-AND-3-SUBSTITUTED CARBOXYLIC ACIDS

(75) Inventors: Li Deng, Waltham, MA (US); Jianfeng Hang, Waltham, MA (US); Liang Tang, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/010,752

(22) Filed: Nov. 5, 2001

(65) Prior Publication Data

US 2002/0151744 A1 Oct. 17, 2002

Related U.S. Application Data

(63) Continuation-in-part of application No. 09/919,371, filed on Jul. 31, 2001.
(60) Provisional application No. 60/222,145, filed on Jul. 31, 2000, and provisional application No. 60/253,172, filed on Nov. 27, 2000.

(51) Int. Cl.[7] .................. C07D 413/12; C07D 413/00; C07C 229/00; C07C 59/48; C07C 59/00
(52) U.S. Cl. .................. 544/97; 544/123; 548/227; 548/317.1; 549/229; 549/379; 562/433; 562/470; 562/553; 562/443; 562/579; 562/580
(58) Field of Search .............. 548/227, 317.1; 549/229, 379; 544/97, 123; 562/433, 470, 553, 579, 443, 580

(56) References Cited

U.S. PATENT DOCUMENTS 5,198,557 A * 3/1993 Giordano et al. ............ 549/513

FOREIGN PATENT DOCUMENTS

| CA | 2329316 | * 11/1999 |
|---|---|---|
| WO | WO 96/28402 | 9/1996 |
| WO | WO 00/09463 | 2/2000 |

OTHER PUBLICATIONS

Romoff et al.; "Urethane–Protected N–carboxyanhydrides (UNCAs) as Unique Reactants for the Study of Intrinsic Racemization Tendencies in Peptide Synthesis", Journal of Peptide Research, 49(4): 281–292, (1997).
Database CAPLUS on STN (Colombus OH, USA), Accession No. 4777908 Preparative Kinetic Resolution of 1–methylindene, Reaction in a Frozen System, Meurling, L. 1974.

(List continued on next page.)

Primary Examiner—Richard L. Raymond
Assistant Examiner—Zachary C. Tucker
(74) Attorney, Agent, or Firm—Dana M. Gordon; Foley Hoag LLP

(57) ABSTRACT

One aspect of the present invention relates to a method for the kinetic resolution of racemic and diastereomeric mixtures of chiral compounds. The critical elements of the method are: a non-racemic chiral tertiary-amine-containing catalyst; a racemic or diastereomeric mixture of a chiral substrate, e.g., a cyclic carbonate or cyclic carbamate; and a nucleophile, e.g., an alcohol, amine or thiol. A preferred embodiment of the present invention relates to a method for achieving the kinetic resolution of racemic and diastereomeric mixtures of derivatives of α- and β-amino, hydroxy, and thio carboxylic acids. In certain embodiments, the methods of the present invention achieve dynamic kinetic resolution of a racemic or diastereomeric mixture of a substrate, i.e., a kinetic resolution wherein the yield of the resolved enantiomer or diastereomer, respectively, exceeds the amount present in the original mixture due to the in situ equilibration of the enantiomers or diastereomers under the reaction conditions prior to the resolution step.

33 Claims, 8 Drawing Sheets

OTHER PUBLICATIONS

International Search Report Completed on Aug. 4, 2002 and mailed on Sep. 9, 2002.

Gottwald and Seebach; "Ring Opening With Kinetic Resolution of Azlactones by Ti–TADDOlates", Tetrahedron 55: 723–738, (1999).

Liang et al.; "Dynamic Kinetic Resolutions Catalyzed by a Planar–Chiral Derivative of DMAP: Enantioselective Synthesis of Protected α–Amino Acids from Racemic Azlactones", J. Org. Chem. 63: 3154–3155, (1998).

Seebach et al.; "Resolution of Racemic Carboxylic Acid derivatives by TI–TADDOLate Mediated Esterification Reactions a General Method for the Preparation of Enantiopure compounds", Tetrahedron 53(22): 7539–7556, (1997).

International Search Report Completed on Dec. 12, 2001, and Mailed on Jan. 2, 2002.

Toyooka et al.; "A Novel and Facile Synthesis of 5–Substituted 1,3–Dioxolane–2,4– Diones Using Trichloromethyl Chloroformate", Hetercycle 29(5): 975–978, (1989).

Lee and Downie, "Sugar Esthers– IV, The Preparation of Chloroesters Under Essentially –Neutral Conditions", Tetrahedron 23: 359–363, (1967).

Mori et al.; "Synthesis of Optically Active Forms of Ipsdienol and Ipsenol", Tetrahedron 35: 933–940, (1979).

Grieco et al.; "Fluoroprostaglandins: Total Synthesis of (+)–13–Fluoroprostaglandin $F_{2\alpha}$ Methyl Ester", J. Org. Chem. 50:3111–3115, (1985).

Kitamura et al.; "Homogeneous Asymmetric Hydrogenetion of Functionalized Ketones", J. Am. Chem. Soc. 110: 629–631, (1988).

Mashima et al.; "Cationic BINAP–RU (II) Halide Complexes: Highly Efficient Catalysts for Stereoselective Asymmetric Hydrogenation of α– and β– Functionalized Ketones", J. Org. Chem. 59: 3064–3076, (1994).

Burk et al.; "Rh– DuPHOS–Catalyzed Enantioselective Hydrogenation of Enol Esters. Application to the Synthesis of Highly Enantioenriched α–Hydroxy Esters and 1,2–Diols", J. Am. Chem. Soc. 120: 4345–4353, (1998).

Wang et al.; "Enantioselective Synthesis of α–Oxocarboxylic Acids to Enantiomerically Enriched α–Hydroxy Carboxylic Acids via Neighboring Group Control", Tetrahedron Letters 39: 5501–5504, (1998).

Huerta et al.; "Dynamic Kinetic Resolution of α–Hydrosy Acid Esters", Optic Letters 2 (8): 1037–1040, (2000).

Daly and Poche, "The Preparation of N–Carboxyanhydrides of α–Amino Acids Using Bs(Trichloromethy)Carbonate", Tetrahedron Letters 29(46):5859–5862, (1988).

Fuller et al; "Urethane–Protected α–Amino Acid N–Carboxyanhydrides and Peptide Synthesis", Biopolymers (Peptide Science), 40: 183–205, (1996).

Corey et al; "Highly Enantioselective Synthesis of Cyclic and Functionalized α– Amino Acids by Means of a Chiral Phase Transfer Catalyst", Tetrahedron Letters 39:5347–5350, (1998).

Corey et al.; "A Rational Approach of Catalytic of Enantioselective Enolate Alkylation Using a Structurally Rigidified and Defined Chiral Quaternary Ammonium Salt Under Phase Transfer Conditions", J. Am. Chem. Soc. 119: 12414–12415, (1997).

Ooi et al.; "Practical Catalytic Enantioselective Synthesis of α,α– Dialkyl–α–amino Acids by Chiral Phase–Transfer Catalysis", J. Am. Chem. Soc. 122: 5228–5229, (2000).

Ooi et al.; "Molecular Design of $C_2$– Symmetric Chiral Phase–Transfer Catalyst for Practical Asymmetric Synthesis of α–Amino Acids", J. Am. Chem. Soc., 121: 6519–6520, (1999).

O'Donnell et al.; "An Efficient Homogeneous Catalytic Enantioselective Synthesis of α0–Amino Acid Derivatives", Tetrahedron Letters 39: 8775–8778, (1998).

Porter et al.; "Ti–Catalyzed Regio– and Enantioselective Synthesis of Unsaturated α–Amino Nitriles, Amides and Acids, Catalyst Identification Through Screening of Parallel Libraries", J. Am. Chem. Soc. 122: 2657–2658, (2000).

Krueger et al.; "Ti–Catalyzed Enantioselective Addition of Cyanide to Imines. A Practical Synthesis of Optically Pure α–Amino Acids", J. Am. Chem. Soc. 121: 4284–4285, (1999).

Sigman and Jacobsen, "Enantioselective Addition of Hydrogen Cyanide to Imines Catalyzed by a Chiral (Salen) Al (III) Complex", J. Am. Chem. Soc. 120: 5315–5316 (1998).

Sigman and Jacobsen; "Schiff Base Catalysts for the Asymmetric Strecker Reaction Identified and Optimized from Parallel Synthetic Libraries", J. Am Chem. Soc. 120: 4901–4902, ( 1998).

Ishitani et al.; "Catalytic Enantioselective Synthesis of α–Aminonitriles with a Novel Zirconium Catalyst", Angew. Chem. Int. ed. 37(22): 3186–3188, (1998).

Corey and Grogan; "Enantioselective Synthesis of α–Amino Nitriles from N–Benzhydryl Imines and HCN with a Chiral Bicyclic Guanidine as Catalyst", Organic Letters, 1(1): 157–160, (1999).

Burke et al.; "Highly Regio– and Enantioselective Catalytic Hydrogenation of Enamides in Conjugated Diene Systems: Synthesis and Application of γ, δ–Unsaturated Amino Acids", J. Am. Chem. Soc. 120: 657–663, (1998).

Ferris et al.; "Catalytic, Enantioselective Alkylation of α–Imino Esters Using Late Transition Phosphine Complexes as Catalysts", J. Am. Chem. Soc., 120: 4548–4549, (1998).

Fang et al.; "Catalytic Approach for the Formation of Optically Active Allyl α– Amino Acids by Addition of Ally Metal Compounds to α–Imino Esters", J. Org. Chem. 64: 4844–4849, (1999).

* cited by examiner

Figure 2
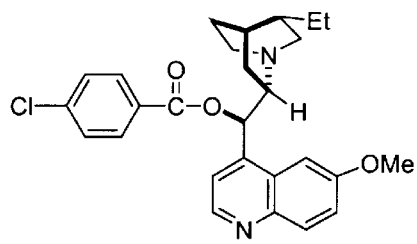
DHQ-CLB
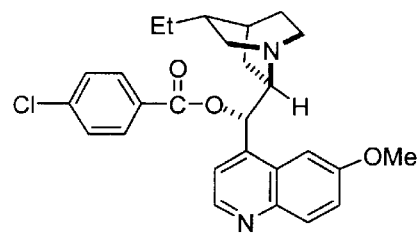
DHQD-CLB
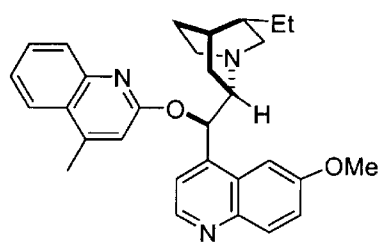
DHQ-MEQ
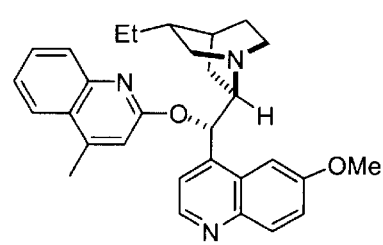
DHQD-MEQ
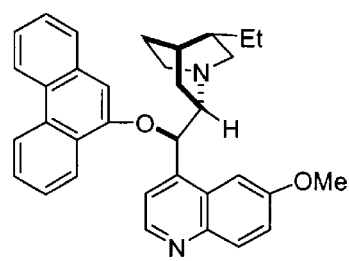
DHQ-AQN
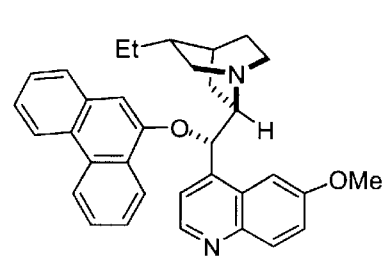
DHQD-AQN
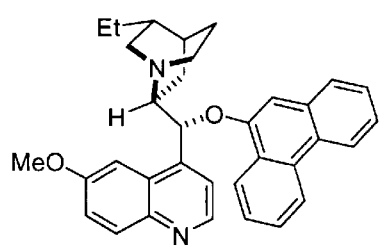
DHQ-PHN
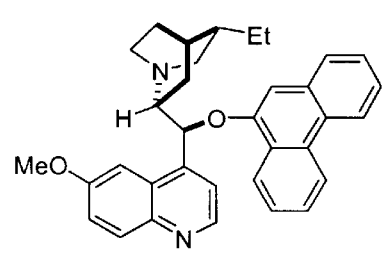
DHQD-PHN Figure 3
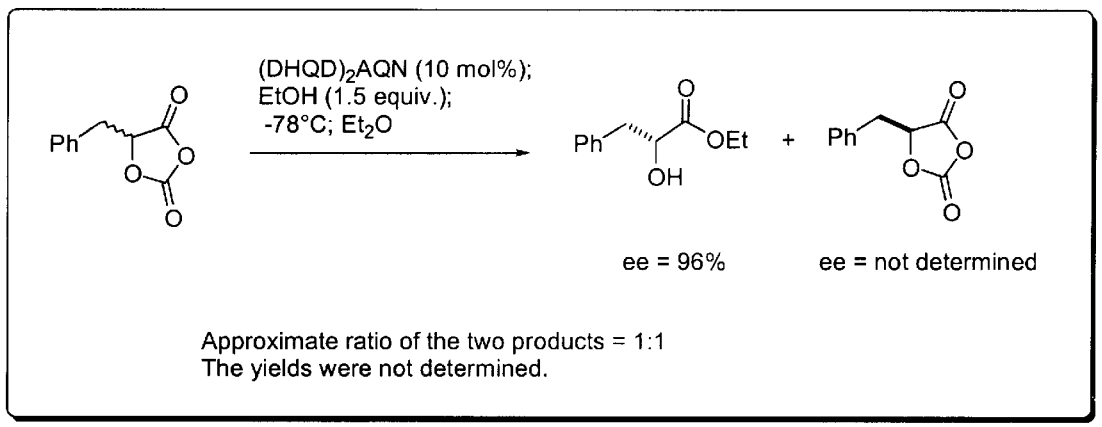
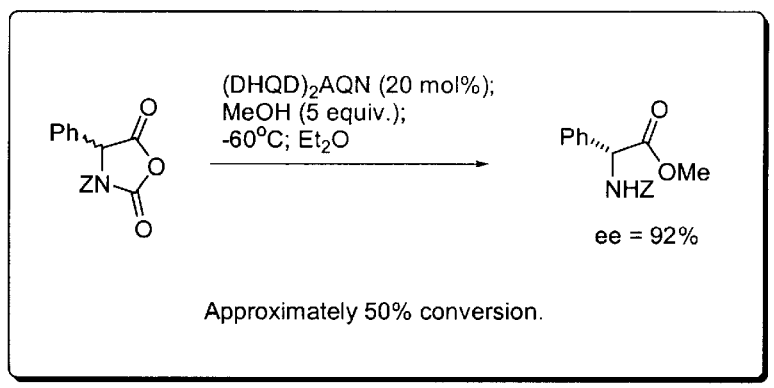

Figure 4

| Substrate | Catalyst | Conv (%) | Product | %ee | Selectivity |
|---|---|---|---|---|---|
| isopropyl cyclic carbonate | (DHQD)₂AQN | 27 | ethyl 2-hydroxy-3-methylbutanoate | 86 | 37 |
| | | 32 | 2-hydroxy-3-methylbutanoic acid | 85.4 | |
| butyl cyclic carbonate | (DHQD)₂AQN | 38 | ethyl 2-hydroxyhexanoate | 96.2 | 156 |
| | | 34 | 2-hydroxyhexanoic acid | 90.8 | |
| benzyl cyclic carbonate | (DHQD)₂AQN | 43 | ethyl 2-hydroxy-3-phenylpropanoate | 96.7 | 224 |
| | | 38 | 2-hydroxy-3-phenylpropanoic acid | 96.6 | |

Figure 5
| Substrate | Catalyst | Conv (%) | Product | %ee | Selectivity |
|---|---|---|---|---|---|
| 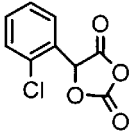 | (DHQD)$_2$AQN | 53.5(conv) | 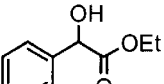 | 89.3 | |
| | | | 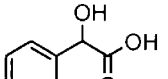 | 50 | |
| 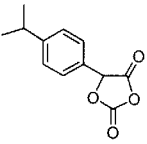 | (DHQD)$_2$AQN | 34 | 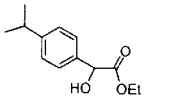 | 94 | 52 |
| | | 40 | 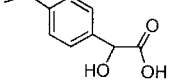 | | |
| 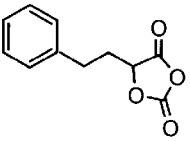 | (DHQD)$_2$AQN | 48 | 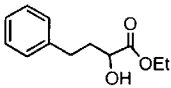 | 92.3 | 70 |
| | | | 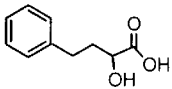 | 85.7 | |

Figure 6

| Substrate | Catalyst | Yield (%) | Product | ee (%) | Temp |
|---|---|---|---|---|---|
| phenyl dioxolane-dione | (DHQD)₂AQN | 78 | ethyl mandelate | 95 | -63 |
| 4-Br-phenyl dioxolane-dione | (DHQD)₂AQN | 80 | ethyl 4-Br-mandelate | 97.5 | -78 |
| 4-Cl-phenyl dioxolane-dione | (DHQD)₂AQN | 65 | ethyl 4-Cl-mandelate | 96.5 | -78 |
| 4-CF₃-phenyl dioxolane-dione | (DHQD)₂AQN | 85 | ethyl 4-CF₃-mandelate | 95 | -78 |
| benzothiophene dioxolane-dione | (DHQD)₂AQN | 78 | ethyl benzothiophene glycolate | 82.6 | -78 |
| 4-F-phenyl dioxolane-dione | (DHQD)₂AQN | 61 | ethyl 4-F-mandelate | 94.6 | -78 |
| 2-naphthyl dioxolane-dione | (DHQD)₂AQN | 70 | ethyl 2-naphthyl glycolate | 88 | -78 |

2 racemic → 3 non-racemic

| Entry | R | P | R'OH | T (C) | Ee of 3 | Yield of 3 |
|---|---|---|---|---|---|---|
| 1 | 2-furyl | Cbz | EtOH | -20 | 96% | 86% |
| 2 | 2,5-dimethylfuryl | Cbz | EtOH | -20 | 96% | 87% |
| 3 | 3-methylthienyl | Cbz | EtOH | -20 | 91% | >90% |
| 4 | 2-thienyl | Cbz | EtOH | -20 | 94% | 94% |
| 5 | 2-thienyl | Cbz | Allyl alcohol | -30 | 90% | 99% |

2  
racemic 3  
non-racemic

| Entry | R | P | R'OH | T (C) | Ee of 3 | Yield of 3 |
|---|---|---|---|---|---|---|
| 1 | Ph-CH₂ (phenyl) | Cbz | Allyl alcohol | rt | 91% | 95% |
| 2 | Ph-CH₂ (phenyl) | Fmoc | Allyl alcohol | rt | 90% | 98% |
| 3 | 4-Cl-C₆H₄-CH₂ | Cbz | Allyl alcohol | rt | 92% | 95% |
| 4 | 4-F-C₆H₄-CH₂ | Cbz | Allyl alcohol | rt | 90% | 95% |
| 5 | 4-F₃C-C₆H₄-CH₂ | Cbz | Allyl alcohol | rt | 90% | 93% |

US 6,562,967 B2

KINETIC RESOLUTIONS OF CHIRAL 2-AND-3-SUBSTITUTED CARBOXYLIC ACIDS

RELATED APPLICATIONS

This application is a continuation-in-part of U.S. patent application Ser. No. 09/919,371, filed Jul. 31, 2001; which claims the benefit of the filing date of U.S. Provisional Patent Application Ser. No. 60/222,145, filed Jul. 31, 2000; and U.S. Provisional Patent Application Ser. No. 60/253,172, filed Nov. 27, 2000.

GOVERNMENT SUPPORT

This invention described herein was supported in part by National Institutes of Health Grant Number NIH GM61591. The U.S. Government has certain rights to this invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages (reviewed in, e.g., Stinson, S. C., *Chem Eng News*, Sep. 28, 1992, pp. 46–79) include the fewer side effects and greater potency often associated with enantiomerically pure compounds.

Traditional methods of organic synthesis were often optimized for the production of racemic materials. The production of enantiomerically pure material has historically been achieved in one of two ways: use of enantiomerically pure starting materials derived from natural sources (the so-called "chiral pool"); and the resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming. Furthermore, resolution often means that the undesired enantiomer is discarded, thus decreasing efficiency and wasting half of the material.

SUMMARY OF THE INVENTION

One aspect of the present invention relates to a method for the kinetic resolution of racemic and diastereomeric mixtures of chiral compounds. The critical elements of the method are: a non-racemic chiral tertiary-amine-containing catalyst; a racemic or diastereomeric mixture of a chiral substrate, e.g., a cyclic carbonate or cyclic carbamate; and a nucleophile, e.g., an alcohol, amine or thiol. A preferred embodiment of the present invention relates to a method for achieving the kinetic resolution of racemic and diastereomeric mixtures of derivatives of α- and β-amino, hydroxy, and thio carboxylic acids. In certain embodiments, the methods of the present invention achieve dynamic kinetic resolution of a racemic or diastereomeric mixture of a substrate, i.e., a kinetic resolution wherein the yield of the resolved enantiomer or diastereomer, respectively, exceeds the amount present in the original mixture due to the in situ equilibration of the enantiomers or diastereomers under the reaction conditions prior to the resolution step.

BRIEF DESCRIPTION OF THE DRAWINGS

FIG. 2 depicts the structures of certain catalysts used in the methods of the present invention, and their abbreviations herein.

FIG. 3 depicts two embodiments of the methods of the present invention.

FIG. 4 tabulates the yields and enantiomeric excesses of the products and unreacted starting materials of kinetic resolutions of various dioxolanediones.

FIG. 5 tabulates the yields and enantiomeric excesses of the products and unreacted starting materials of kinetic resolutions of various dioxolanediones.

FIG. 6 tabulates the yields and enantiomeric excesses of the products and unreacted starting materials of kinetic resolutions of various dioxolanediones.

DETAILED DESCRIPTION OF THE INVENTION

Figure 1:
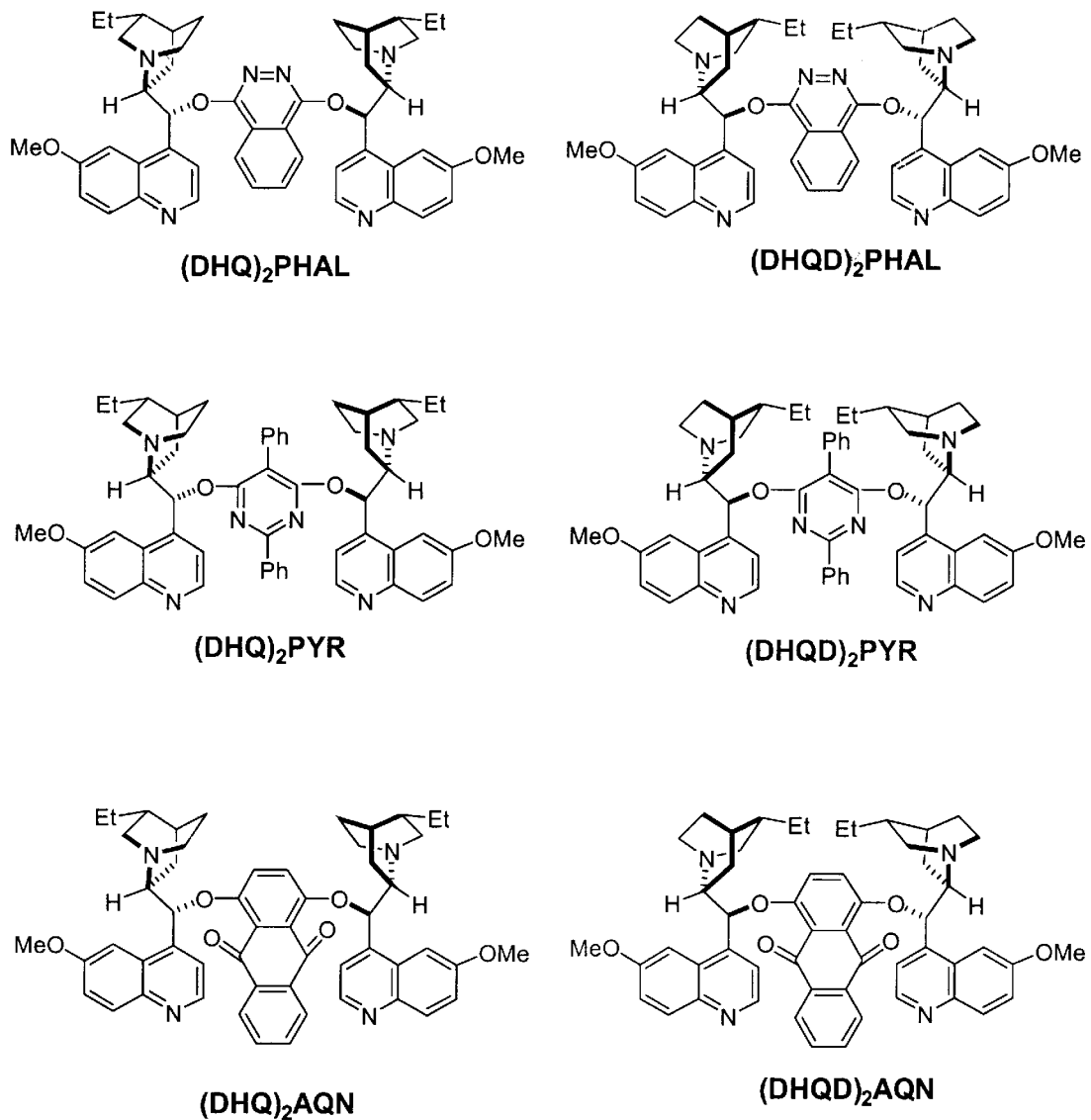
FIG. 1 depicts the structures of certain catalysts used in the methods of the present invention, and their abbreviations herein.

The ability to selectively transform a racemic or diastereomeric mixture of a chiral compound to an enantiomerically- or diastereomerically-enriched or an enantiomerically- or diastereomerically-pure chiral compound has broad applicability in the art of organic chemistry, especially in the agricultural and pharmaceutical industries, as well as in the polymer industry. As described herein, the present invention relates to methods for the kinetic resolution of racemic and diastereomeric mixtures of chiral compounds. As set forth in greater detail below, the primary constituents of the methods are: a non-racemic chiral tertiary-amine-containing catalyst; a racemic or diastereomeric mixture of a chiral substrate, e.g., a cyclic carbonate or cyclic carbamate; and a nucleophile, e.g., an alcohol or thiol. In the methods of the present invention, said nucleophile selectively attacks one of the diastereomeric transition states or intermediates formed from the catalyst and substrate, generating an enantiomerically- or diastereomerically-enriched or an enantiomerically- or diastereomerically-pure chiral product.

Catalytic Asymmetric Synthesis of α-Hydroxy Carboxylic Acids

Racemic 5-alkyl-1,3-dioxolane-2,4-diones (2) can be prepared readily from the corresponding racemic α-hydroxy carboxylic acids (1). Toyooka, K. et al. *Heterocycles* 1989, 29, 975–978. The successful development of an efficient kinetic resolution of 2 has lead to an attractive catalytic preparation of chiral non-racemic α-hydroxy carboxylic acid derivatives, which are versatile chiral building blocks in asymmetric synthesis (See Scheme 1). Lee, J. B. et al. *Tetrahedron* 1967, 23, 359–363; Mori, K. et al. *Tetrahedron* 1979, 35, 933–940; and Grieco, P. A. et al. *J. Org. Chem.* 1985, 50, 3111–3115.

Scheme 1

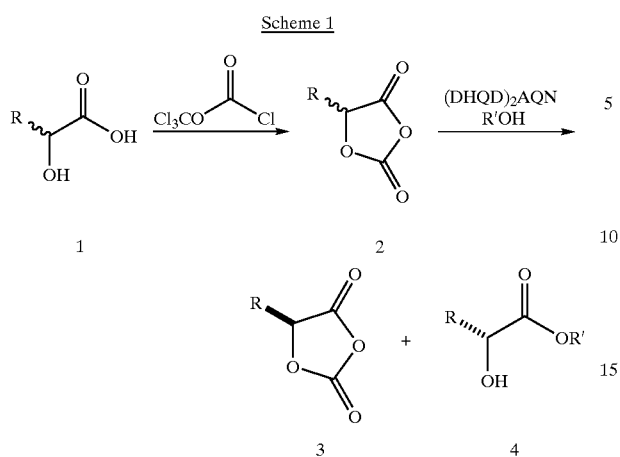

For example, we have investigated the kinetic resolution of 5-phenyl-1,3-dioxolane-2,4-dione (5), using cinchona-alkaloid-catalyzed alcoholysis. As illustrated in Scheme 2, we found that the racemic starting material (5) can be converted to a single product in 65% yield in excellent enantiomeric excess (97%). Apparently, the kinetic resolution of 5 occurs in the most desirable fashion, i.e., dynamic kinetic resolution. Rapid epimerization at the stereocenter of the starting material allows the establishment of an equilibrium between the two enantiomers of the starting material (5a and 5b). The coupling of this equilibrium with a selective conversion of one of the two enantiomers leads to the conversion of the racemic mixture to a single product with a yield greater than 50% and in high enantiomeric excess. Acting as both a Bronsted base and a Lewis base, the cinchona alkaloid appears to catalyze both the epimerization and the alcoholysis reactions. Based on the observed enantiomeric excess of the product, the selectivity factor ($k_{fast}/k_{slow}$) for the reaction is greater than 50. As demonstrated herein, the dynamic kinetic resolution overcomes traditional drawbacks associated with a standard kinetic resolution, such as a maximum yield of 50% and the eventual need to separate a mixture of compounds, e.g., the product from unreacted starting material. All signs indicate that this reaction can be developed into one of the most practical methods for the asymmetric synthesis of optically active α-hydroxy carboxylic acid derivatives. Kitamura, M. et al. *J. Am. Chem. Soc.* 1988, 110, 629–631; Mashima, K. et al. *J. Org. Chem.* 1994, 59, 3064–3076; Burk, M. J. et al. *J. Am. Chem. Soc.* 1998, 120, 4345–4353; Wang, Z. et al. *Tetrahedron Lett.* 1998, 39, 5501–5504; Chiba, T. et al. *Tetrahedron Lett.* 1993, 34, 2351–2354; and Huerta, F. F. et al. *Org. Lett.* 2000, 2, 1037–1040.

Scheme 2

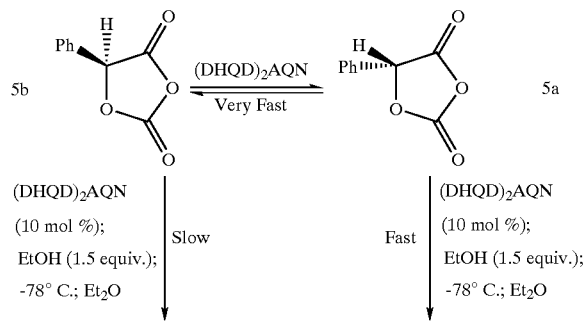

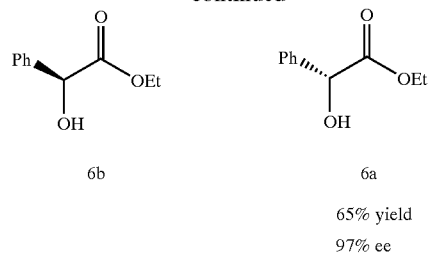

65% yield
97% ee

Catalytic Asymmetric Synthesis of α-Amino Carboxylic Acids

Acyl transfer reactions utilize cheap reagents to transform readily available starting materials into useful and easily purified products. These characteristics in combination with high enantioselectivity have enabled acyl transfer reactions catalyzed by enzymes such as lipase and esterase to become highly valuable methods for asymmetric synthesis. The development of synthetic catalysts to mimic lipase/esterase with the goal of further expanding the scope and synthetic utility of asymmetric acyl transfer catalysis is of both conceptual and practical significances for asymmetric catalysis. Although several effective synthetic catalysts for the kinetic resolution of racemic alcohols have recently emerged, efforts to develop small molecule-catalyzed kinetic resolutions of racemic carbonyl derivatives have met with limited success despite their great potential in asymmetric synthesis. We report here an exceedingly general and highly enantioselective kinetic resolution of urethane-protected α-amino acid N-Carboxy Anhydrides (UNCA) that generates optically active α-amino acids derivatives suitable for further synthetic elaborations such as peptide synthesis.

Encouraged by our discovery of highly enantioselective alcoholysis for the desymmetrization of meso anhydrides, we became particularly interested in the kinetic resolution of racemic carbonyl compounds such as the urethane-protected α-amino acid N-carboxy anhydrides (UNCA, 2) via cinchona alkaloid-catalyzed alcoholysis alcoholysis to generate optically active carbamate-protected α-amino acids derivatives (Scheme 3). UNCAs (2) are easily accessible from racemic amino acids (1), stable for long term storage. Their alcoholysis generates the carbamate-protected amino ester 3 and the environmentally benign $CO_2$. Moreover, the remaining enantiomerically enriched UNCA (2a) after the kinetic resolution can be converted to the carbamate-protected amino acid (4) by hydrolysis (Scheme 3). The reaction mixture, consisting of the Brønsted basic amine catalyst, the acidic amino acid (4) and the neutral amino ester (3), can be separated using simple procedures to give 3 and 4 as well as the recovered catalyst in desired chemical and optical purity.

Scheme 3

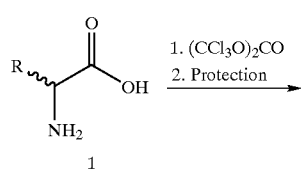

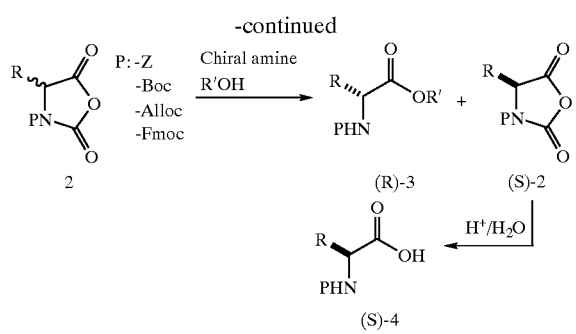

Racemic N-Cbz-phenylalanine NCA (2a), prepared from racemic phenyl alanine in 72% yield for two steps, was employed as a model substrate in the initial evaluation of key reaction parameters to establish optimal conditions for the kinetic resolution. Reaction of 2a with methanol (0.55 equiv) at room temperature in ether in the presence of (DHQD)$_2$AQN (10 mol %) and molecular sieves (4A) provided the desired methyl ester 3a in 82% ee at 40% reaction conversion, indicating that the kinetic resolution proceeded with a selectivity factor (s) of 16 (entry 1, Table 1). Following this promising lead, we subsequently found that the enantioselectivity of the kinetic resolution can be dramatically improved by carrying out the (DHQD)$_2$AQN-catalyzed alcoholysis at low temperature. At −60° C. the enantioselectivity of the kinetic resolution was found to reach a level (s=79, entry 2, Table 1) comparable to that of an efficient enzyme-catalyzed kinetic resolution.

A variety of natural and modified cinchona alkaloids were screened for their abilities to mediate the kinetic resolution of 2a via alcoholysis. The results are summarized in Table 1. While (DHQD)$_2$AQN, a modified biscinchona alkaloid, stands as the most effective in our catalyst screening, a modified monocinchona alkaloid, DHQD-PHN, is also found to be a highly effective catalyst (entry 3, Table 1). Particularly notable, however, is the finding that an excellent enantioselectivity could be achieved with quinidine, a natural cinchona alkaloid (entry 4, Table 1). Interestingly, under the same condition, reactions with other closely related chiral and achiral amines, including (DHQD)$_2$ PYR, (DHQD)$_2$PHAL, DHQD-MEQ, DHQD-CLB and quinuclidine, gave only minuscule conversions (1–4%).

The practical features of the kinetic resolution were demonstrated in a preparative scale resolution of 2a (4.0 mmol). The modified cinchona alkaloid-catalyzed alcoholysis of 2a proceeded cleanly to allow the isolation of both ester 3a and acid 4a in nearly quantitative yields and the quantitative recovery of the catalyst in pure form using a simple extractive procedure (Table 2). The recovered catalyst can be used directly for another preparative-scale resolution of 2a, showing no detectable deterioration in catalytic activity and selectivity (Table 2).

TABLE 1

Kinetic Resolution of UNCA 2a with Cinchona Alkaloids[a]

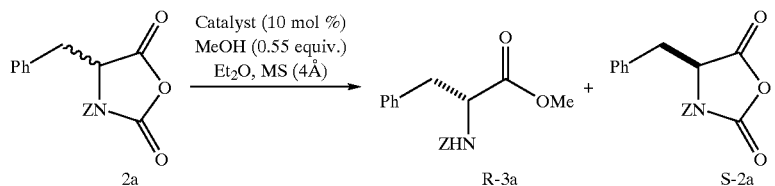

| Entry | Catalyst | T/° C. | Conv/%[b] | ee of 3a/%[c,d] | s[e] |
|---|---|---|---|---|---|
| 1 | A | 25 | 42 | 80 | 16 |
| 2 | A | −60 | 50 | 92 | 79 |
| 3 | B | −60 | 45 | 91 | 47 |
| 4 | C | −60 | 44 | 86 | 27 |

[a]The reaction was performed with 2a (0.1 mmol) in ether (7.0 mL).
[b]Determined by GC analysis, see Supporting Information.
[c]Determined by HPLC analysis, see Supporting Information.
[d]The absolute configuration of 3a was determined by comparison of its sign of optical rotation with the literature value; see Supporting Information.
[e]The selectivity factor s was calculated using the equation $s = k_F/k_s = \ln[1 - C(1 + ee)]/\ln[1 - C(1 - ee)]$, where ee is the percent enantiomeric excess of the product (3a) and C is the conversion.

Catalyst A = (DHQD)$_2$AQN

Catalyst B = DHQD-PHN

Catalyst C = Quinidine

TABLE 2

Preparative Scale Kinetic Resolution of 2a with Recycled (DHQD)₂AQN

| Cycle | Conv[a] | ee[b] (yield[c])/% | | s |
|---|---|---|---|---|
| | | 3a | 4a | |
| 1 | 51 | 93 (48) | 97 (48) | 114 |
| 2 | 52 | 91 (49) | 98 (47) | 97 |

[a]The conversion, calculated using the equation: $C = 100 \times ee_{2a}/(ee_{3a} + ee_{2a})$, is consistent with that determined experimentally, see supporting information
[b]For ee analysis and absolute configuration determination, see Supporting Information.
[c]Isolated yield.

The scope of the reaction was found to be highly general. Clean kinetic resolutions of extraordinarily high enantioselectivities were attainable with an extensive range of UNCAs (Table 3). Following the same extractive procedure used for the isolation of 3a and 4a, the optically active α-amino esters 3 and amino acids 4 derived from kinetic resolutions of racemic 2 were routinely obtained in a combined yield of greater than 90%. Both α-alkyl- and aryl-substituted UNCAs were resolved with exceptional enantioselectivities. The presence of heteroatoms and heterocycle in the substrates has no negative effect on the efficiency of the kinetic resolution. Even with a substrate bearing a α-branched alkyl side chain, the resolution can be accomplished with a synthetically useful enantioselectivity at 0° C. (entry 8, Table 3). Furthermore, the reaction is remarkably tolerant of structural variations of the protecting group, thus permitting the efficient syntheses of CBz-, Alloc-, Boc-, and even the base-sensitive Fmoc-protected amino acids and esters in high optical purity and excellent yields. Among all the cases examined, (R)-3 and (S)-4 were obtained consistently from the (DHQD)₂AQN-catalyzed kinetic resolution of racemic-2 (a–c, e, g–m).

TABLE 3

Kinetic Resolution of UNCA (2) via Modified Cinchona Alkaloids-Catalyzed Alcoholysis[a]

| | UNCA 2 | | temp | Time | conv | ee[b] (yield)/%[c] | | |
|---|---|---|---|---|---|---|---|---|
| entry | R | P | (° C.) | (h) | (%) | 4 | 3 | S |
| 1 | a PhCH₂[d] | Z | −60 | 17 | 51 | 97 (48) | 93 (48) | 114 |
| 2 | b 4-F-C₆H₄CH₂ | Z | −78 | 31 | 50 | 92 (42) | 92 (48) | 79 |
| 3 | c 4-Cl-C₆H₄CH₂ | Z | −60 | 18 | 52 | 97 (43) | 88 (52) | 59 |
| 4 | d 4-Br-C₆H₄CH₂ | Z | −78 | 45 | 53 | 97[g] (39) | 87[g] (51) | 66 |
| 5 | e 2-thienylmethyl | Z | −78 | 37 | 50 | 94 (47)[h] | 94 (49)[h] | 115 |
| 6 | f CH₃(CH₂)₅ | Z | −60 | 72 | 51 | 94[g] (42) | 91[g] (49) | 78 |
| 7 | g BnOCH₂ | Z | −78 | 22 | 51 | 91 (44) | 89 (49) | 58 |
| 8 | h (CH₃)₂CH[e] | Z | 0 | 16 | 59 | 96 (40) | 67 (58) | 19 |
| 9 | i Ph[f] | Z | −78 | 85 | 46 | 84 (46) | 97 (45) | 170 |
| 10 | j 4-MeO-C₆H₄[f] | Z | −78 | 25 | 56 | 95 (43)[h] | 74 (56)[h] | 23 |
| 11 | k PhCH₂ | Fmoc | −78 | 46 | 51 | 96 (47) | 92 (50) | 93 |
| 12 | l PhCH₂ | Boc | −40 | 15 | 59 | 98 (41) | 67 (56) | 22 |
| 13 | m PhCH₂ | Alloc | −60 | 15 | 50 | 91 (45) | 91 (45) | 67 |
| 14 | n PhCH₂CH₂ | Alloc | −60 | 36 | 54 | 96[g] (41) | 81[g] (53) | 35 |

[a]Unless otherwise noted, the reaction was performed by treatment of 2 (0.1 mmol) with (DHQD)₂AQN (10 mol %) and methanol (0.52–1.0 eq.) in ether (7.0 mL).
[b]For details of ee analysis and absolute configuration determination for 3 and 4, see Supporting Information.
[c]Unless otherwise noted, Isolated yield using an extractive procedure.
[d]The reaction was performed with 4.0 mmol of 2a.
[e]The reaction was catalyzed by DHQD-PHN (20 mol %).
[f]0.55 eq of ethanol was used.
[g]The absolute configuration was not determined.
[h]isolated yield using a chromatographic purification.

Importantly, our results indicate that we have discovered a practical method for the preparation of optically pure chiral α-amino acids. Moreover, we believe our method compares favorably to other catalytic methods for chiral amino acid synthesis. See Corey, E. J. et al. *Tetrahedron Lett.* 1998, 39, 5347–5350; Corey, E. J. et al. *J. Am. Chem. Soc.* 1997, 119, 12414–12415; Ooi, T. et al. *J. Am. Chem. Soc.* 2000, 122, 5228–5229; Ooi, T. et al. *J. Am. Chem. Soc.* 1999, 121, 6519–6520; O'Donnell, M. J. et al. *Tetrahedron Lett.* 1998, 39, 8775–8778; Porter, J. R. et al. *J. Am. Chem. Soc.* 2000, 122, 2657–2658; Krueger, C. A. et al. *J. Am. Chem. Soc.* 1999, 121, 4284–4285; Sigman, M. S. et al. *J. Am. Chem. Soc.* 1998, 120, 5315–5316; Sigman, M. S. et al. *J. Am. Chem. Soc.* 1998, 120, 4901–4902; Ishtani, H. et al. *Angew. Chem. Int. Ed.* 1998, 37, 3186–3188; Corey, E. J. et al. *Org. Lett.* 1999, 1, 157–160; Burk, M. J. et al. *J. Am. Chem. Soc.* 1998, 120, 657–663; Ferraris, D. et al. *J. Am. Chem. Soc.* 1998, 120, 4548–4549; and Fang, X. et al. *J. Org. Chem.* 1999, 64, 4844–4849. Further, our method generates amino acids protected with a group that is commonly used in peptide synthesis, i.e., the so-called Z or Cbz group. Other catalytic methods developed for the preparation of optically active α-amino acids often require special protecting groups that must ultimately be converted to a more suitable protecting group, such as Cbz. Finally, the asymmetric catalyst, e.g., (DHQD)$_2$AQN, can be recycled via simple acid washing and extraction.

In sum, we have discovered the first effective and general nonenzymatic catalytic method for the asymmetric synthesis of α-amino acids via a kinetic resolution strategy. With its extraordinary enantioselectivity and generality, the kinetic resolution of UNCA (2) via asymmetric alcoholysis catalyzed by cinchona alkaloids provides a highly enantioselective and reliable catalytic method for the preparation of optically active amino acid derivatives that are suitably protected for direct further synthetic elaborations. The reaction utilizes readily accessible substrates, cheap reagents, commercially available as well as fully recyclable catalysts, and simple experimental protocols involving no chromatography.

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like.

The terms "electrophilic atom", "electrophilic center" and "reactive center" as used herein refer to the atom of the substrate that is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% enantiomeric excess (ee)A=(% enantiomer A)−(% enantiomer B)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantimerically-enriched unreacted substrate. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "alkenyl" and "alkynyl" refer to unsaturated aliphatic groups analogous in length and possible substitution to the alkyls described above, but which contain at least one double or triple carbon—carbon bond, respectively.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

an be represented by the general formula:

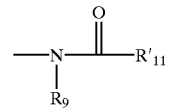

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

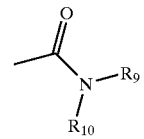

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are as defined above. Representative alkylthio groups include methylthio, ethyl thio, and the like.

The term "carbonyl" is art recognized and includes such moieties as can be represented by the general formula:

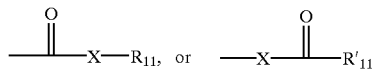

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

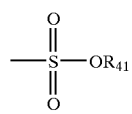

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

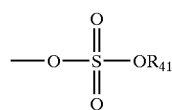

in which $R_{41}$ is as defined above.

The term "sulfonylamino" is art recognized and includes a moiety that can be represented by the general formula:

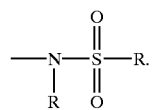

The term "sulfamoyl" is art-recognized and includes a moiety that can be represented by the general formula:

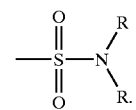

The term "sulfonyl", as used herein, refers to a moiety that can be represented by the general formula:

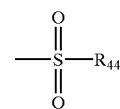

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

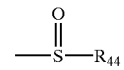

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986–87, inside cover.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Catalysts of the Invention

The catalysts employed in the subject methods are non-racemic chiral tertiary amines, phosphines and arsines which present an asymmetric environment, causing differentiation between the two enantiomers or diastereomers of the substrate mixture, i.e., the chiral non-racemic catalyst preferentially reacts with one enantiomer or diastereomer of the substrate mixture. In preferred embodiments, catalysts employed in the subject methods are non-racemic chiral tertiary amines, e.g., cinchona alkaloids. In general, catalysts useful in the methods of the present invention can be characterized in terms of a number of features. For instance, in preferred embodiments, the catalysts comprise asymmetric bicyclic or polycyclic scaffolds incorporating a tertiary amine moiety which provide a rigid or semi-rigid environment near the amine nitrogen. This feature, through imposition of structural rigidity on the amine nitrogen in proximity to one or more asymmetric centers present in the scaffold, contributes to the creation of a meaningful difference in the energies of the corresponding diastereomeric transitions states for the overall transformation. Furthermore, the choice of substituents on the tertiary amine may also effect catalyst reactivity; in general, bulkier substituents are found to provide higher catalyst turnover numbers.

A preferred embodiment for each of the embodiments described above provides a catalyst having a molecular weight less than 2,000 g/mol, more preferably less than 1,000 g/mol, and even more preferably less than 500 g/mol. Additionally, the substituents on the catalyst can be selected to influence the solubility of the catalyst in a particular solvent system. FIGS. 2 and 3 depict preferred embodiments of tertiary amine catalysts used in the methods of the present invention.

As mentioned briefly above, the choice of catalyst substituents can also effect the electronic properties of the catalyst. Substitution of the catalyst with electron-rich (electron-donating) moieties (including, for example, alkoxy or amino groups) may increase the electron density of the catalyst at the tertiary amine nitrogen, rendering it a stronger Bronsted and/or Lewis base. Conversely, substitution of the catalyst with electron-poor moieties (for example, chloro or trifluoromethyl groups) can result in lower electron density of the catalyst at the tertiary amine nitrogen, rendering it a weaker Bronsted and/or Lewis base. To summarize this consideration, the electron density of the catalyst can be important because the electron density at the tertiary amine nitrogen will influence the Lewis basicity of the nitrogen and its nucleophilicity. Choice of appropriate substituents thus makes possible the "tuning" of the reaction rate and the stereoselectivity of the reaction.

Methods of the Invention—Catalyzed Reactions

One aspect of the present invention provides a method for the kinetic resolution of racemic or diastereomeric mixtures of a substrate, yielding a single enantiomer or diastereomer, respectively, of the product or unreacted substrate or both. The critical elements of the method are: a non-racemic chiral tertiary-amine-containing catalyst; a racemic or diastereomeric mixture of a chiral substrate, e.g., a cyclic carbonate or cyclic carbamate; and a nucleophile, e.g., an alcohol or thiol. An advantage of this invention is that enantiomerically or diastereomerically enriched substrates, products or both can be prepared from racemic or diastereomeric mixtures of substrates.

In certain embodiments, the methods of the present invention achieve dynamic kinetic resolution of a racemic or diastereomeric mixture of a substrate, i.e., a kinetic resolution wherein the yield of the resolved enantiomer or diastereomer, respectively, exceeds the amount present in the original mixture due to the in situ equilibration of the enantiomers or distereomers under the reaction conditions prior to the resolution step. An advantage of the dynamic kinetic resolution methods is that yield losses associated with the presence of an undesired enantiomer or diastereomer can be substantially reduced or eliminated altogether. Preferred embodiments of the present invention relate to methods for achieving the kinetic resolution of racemic and diastereomeric mixtures of derivatives of α-amino- and β-amino, hydroxy, and thio carboxylic acids.

In general, the invention features a stereoselective ring opening process which comprises combining a nucleophile, e.g., an alcohol, thiol or amine, a racemic or diastereomeric mixture of a chiral cyclic substrate, e.g., prepared from an α- or β-heteroatom-substituted carboxylic acid, and a catalytic amount of non-racemic chiral tertiary-amine-containing catalyst. The cyclic substrate will include the carboxylate carbon of the precursor α- or β-heteroatom-substituted carboxylic acid, which carboxylate carbon is susceptible to tandem attack by the tertiary-amine-containing catalyst and nucleophile. The combination is maintained under conditions appropriate for the chiral tertiary-amine-containing catalyst to catalyze the kinetic resolution of the racemic or diastereomeric mixture of the substrate. The methods can also be applied to dynamic kinetic resolutions, e.g., wherein the yield of the enantiomerically pure product from a kinetic resolution of a racemic substrate exceeds 50% due to in situ equilibration of the enantiomers of the substrate prior to attack of the catalyst at said carboxylate carbon. Dynamic kinetic resolution methods are preferred.

In the non-dynamic kinetic resolution methods, as applied to a racemic substrate, one enantiomer can be recovered as unreacted substrate while the other is transformed to the desired product. Of course, one of ordinary skill in the art will recognize that the desired product of a kinetic resolution can be the enantiomer or diastereomer that reacts, the enantiomer or diastereomer that does not react, or both. One significant advantage of the methods of the present invention is the ability to use inexpensive racemic or diastereomeric mixtures of the starting materials, rather than expensive, enantiomerically or diastereomerically pure starting compounds.

The processes of this invention can provide optically active products with very high stereoselectivity, e.g., enantioselectivity or diastereoselectivity. In preferred embodiments of the subject kinetic resolutions, the enantiomeric excess of the unreacted substrate or product or both is preferably greater than 50%, more preferably greater than 75% and most preferably greater than 90%. The processes of this invention can also be carried out under reaction conditions suitable for commercial use, and typically proceed at reaction rates suitable for large-scale operations.

Further, the chiral products made available by the kinetic resolution methods of this invention can undergo further reaction(s) to afford desired derivatives thereof. Such permissible derivatization reactions can be carried out in accordance with conventional procedures known in the art. For example, potential derivatization reactions include esterification, N-alkylation of amides, and the like. The invention expressly contemplates the preparation of end-products and synthetic intermediates which are useful for the preparation or development or both of pharmaceuticals, e.g., cardiovascular drugs, non-steroidal anti-inflammatory drugs, central nervous system agents, and antihistaminics.

In certain embodiments, the present invention relates to a method of performing a kinetic resolution of a racemic mixture or a diastereomeric mixture of a chiral substrate, comprising the step of combining a racemic mixture or a diastereomeric mixture of a chiral substrate with a nucleophile, in the presence of a chiral non-racemic catalyst, wherein said chiral non-racemic catalyst catalyzes the addition of said nucleophile to said chiral substrate to give a chiral product or unreacted chiral substrate or both enriched in one enantiomer or diastereomer.

In certain embodiments, the present invention relates to the aforementioned method of performing a kinetic resolution, wherein said kinetic resolution is dynamic.

In certain embodiments, the present invention relates to the aforementioned method of performing a kinetic resolution, wherein said nucleophile is an alcohol, amine or thiol.

In certain embodiments, the present invention relates to the aforementioned method of performing a kinetic resolution, wherein said chiral non-racemic catalyst is a tertiary amine, phosphine or arsine.

In certain embodiments, the present invention relates to the aforementioned method of performing a kinetic resolution, wherein said chiral non-racemic catalyst is a tertiary amine.

In certain embodiments, the present invention relates to the aforementioned method of performing a kinetic resolution, wherein said chiral non-racemic catalyst is a cinchona alkaloid.

In certain embodiments, the present invention relates to the aforementioned method of performing a kinetic resolution, wherein said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

In certain embodiments, the present invention relates to the aforementioned method of performing a kinetic resolution, wherein said substrate comprises a single asymmetric carbon.

In certain embodiments, the present invention relates to the aforementioned method of performing a kinetic resolution, wherein said nucleophile is an alcohol, amine or thiol; said chiral non-racemic catalyst is a tertiary amine, phosphine or arsine; and said substrate comprises a single asymmetric carbon.

In certain embodiments, the present invention relates to the aforementioned method of performing a kinetic resolution, wherein said nucleophile is an alcohol, amine or thiol; said chiral non-racemic catalyst is a tertiary amine; and said substrate comprises a single asymmetric carbon.

In certain embodiments, the present invention relates to the aforementioned method of performing a kinetic resolution, wherein said nucleophile is an alcohol, amine or thiol; said chiral non-racemic catalyst is a cinchona alkaloid; and said substrate comprises a single asymmetric carbon.

In certain embodiments, the present invention relates to the aforementioned method of performing a kinetic resolution, wherein said nucleophile is an alcohol, amine or thiol; said chiral non-racemic catalyst is quinidine, (DHQ)₂PHAL, (DHQD)₂PHAL, (DHQ)₂PYR, (DHQD)₂PYR, (DHQ)₂AQN, (DHQD)₂AQN, DHQ-CLB, DHQD-CLB, DHQ-MEQ, DHQD-MEQ, DHQ-AQN, DHQD-AQN, DHQ-PHN, or DHQD-PHN; and said substrate comprises a single asymmetric carbon.

In certain embodiments, the present invention relates to the aforementioned method of performing a kinetic resolution, wherein the enantiomeric or diastereomeric excess of the product or unreacted substrate is greater than about 50%.

In certain embodiments, the present invention relates to the aforementioned method of performing a kinetic resolution, wherein the enantiomeric or diastereomeric excess of the product or unreacted substrate is greater than about 70%.

In certain embodiments, the present invention relates to the aforementioned method of performing a kinetic resolution, wherein the enantiomeric or diastereomeric excess of the product or unreacted substrate is greater than about 90%.

In certain embodiments, the present invention relates to a method of kinetic resolution represented by Scheme 1:

Scheme 1

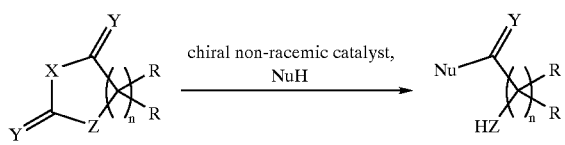

wherein

X represents NR', O, or S;

Y represents independently for each occurrence O or S;

Z represents NR', O, or S;

R represents independently for each occurrence hydrogen, or optionally substituted alkyl, aryl, heteroaryl, aralkyl, or heteroaralkyl;

R' represents independently for each occurrence R, formyl, acyl, sulfonyl, —CO₂R, or —C(O)NR₂;

the substrate and the product are chiral;

NuH represents water, an alcohol, a thiol, an amine, a β-keto ester, a malonate, or the conjugate base of any of them;

chiral non-racemic catalyst is a chiral non-racemic tertiary amine, phosphine, or arsine;

n is 1 or 2; and when said method is completed or interrupted, the enantiomeric excess or diastereomeric excess of the unreacted substrate is greater than that of the substrate prior to the kinetic resolution, the enantiomeric excess or diastereomeric excess of the product is greater than zero, or both.

In certain embodiments, the kinetic resolution method of the present invention is represented by Scheme 1 and the attendant definitions, wherein X is O.

In certain embodiments, the kinetic resolution method of the present invention is represented by Scheme 1 and the attendant definitions, wherein Y is O.

In certain embodiments, the kinetic resolution method of the present invention is represented by Scheme 1 and the attendant definitions, wherein NuH represents an alcohol, a thiol, or an amine.

In certain embodiments, the kinetic resolution method of the present invention is represented by Scheme 1 and the attendant definitions, wherein NuH represents an alcohol.

In certain embodiments, the kinetic resolution method of the present invention is represented by Scheme 1 and the attendant definitions, wherein said chiral non-racemic catalyst is a chiral non-racemic tertiary amine.

In certain embodiments, the kinetic resolution method of the present invention is represented by Scheme 1 and the attendant definitions, wherein said chiral non-racemic catalyst is a cinchona alkaloid.

In certain embodiments, the kinetic resolution method of the present invention is represented by Scheme 1 and the attendant definitions, wherein said chiral non-racemic catalyst is quinidine, (DHQ)₂PHAL, (DHQD)₂PHAL, (DHQ)₂PYR, (DHQD)₂PYR, (DHQ)₂AQN, (DHQD)₂AQN, DHQ-CLB, DHQD-CLB, DHQ-MEQ, DHQD-MEQ, DHQ-AQN, DHQD-AQN, DHQ-PHN, or DHQD-PHN.

In certain embodiments, the kinetic resolution method of the present invention is represented by Scheme 1 and the attendant definitions, wherein X is O; and Y is O.

In certain embodiments, the kinetic resolution method of the present invention is represented by Scheme 1 and the attendant definitions, wherein X is O; Y is O; and NuH represents an alcohol, a thiol, or an amine.

In certain embodiments, the kinetic resolution method of the present invention is represented by Scheme 1 and the attendant definitions, wherein X is O; Y is O; and NuH represents an alcohol.

In certain embodiments, the kinetic resolution method of the present invention is represented by Scheme 1 and the attendant definitions, wherein X is O; Y is O; and said chiral non-racemic catalyst is a chiral non-racemic tertiary amine.

In certain embodiments, the kinetic resolution method of the present invention is represented by Scheme 1 and the attendant definitions, wherein X is O; Y is O; and said chiral non-racemic catalyst is a cinchona alkaloid.

In certain embodiments, the kinetic resolution method of the present invention is represented by Scheme 1 and the attendant definitions, wherein X is O; Y is O; and said chiral non-racemic catalyst is quinidine, (DHQ)₂PHAL, (DHQD)₂PHAL, (DHQ)₂PYR, (DHQD)₂PYR, (DHQ)₂AQN, (DHQD)₂AQN, DHQ-CLB, DHQD-CLB, DHQ-MEQ, DHQD-MEQ, DHQ-AQN, DHQD-AQN, DHQ-PHN, or DHQD-PHN.

In certain embodiments, the kinetic resolution method of the present invention is represented by Scheme 1 and the attendant definitions, wherein X is O; Y is O; NuH represents an alcohol; and said chiral non-racemic catalyst is a chiral non-racemic tertiary amine.

In certain embodiments, the kinetic resolution method of the present invention is represented by Scheme 1 and the attendant definitions, wherein X is O; Y is O; NuH represents an alcohol; and said chiral non-racemic catalyst is a cinchona alkaloid.

In certain embodiments, the kinetic resolution method of the present invention is represented by Scheme 1 and the attendant definitions, wherein X is O; Y is O; NuH represents an alcohol; and said chiral non-racemic catalyst is quinidine, (DHQ)₂PHAL, (DHQD)₂PHAL, (DHQ)₂PYR, (DHQD)₂PYR, (DHQ)₂AQN, (DHQD)₂AQN, DHQ-CLB, DHQD-CLB, DHQ-MEQ, DHQD-MEQ, DHQ-AQN, DHQD-AQN, DHQ-PHN, or DHQD-PHN.

In certain embodiments, the kinetic resolution method of the present invention is represented by Scheme 1 and the attendant definitions, wherein the enantiomeric or diastereomeric excess of the product or unreacted substrate is greater than about 50%.

In certain embodiments, the kinetic resolution method of the present invention is represented by Scheme 1 and the attendant definitions, wherein the enantiomeric or diastereomeric excess of the product or unreacted substrate is greater than about 70%.

In certain embodiments, the kinetic resolution method of the present invention is represented by Scheme 1 and the attendant definitions, wherein the enantiomeric or diastereomeric excess of the product or unreacted substrate is greater than about 90%.

In certain embodiments, the present invention relates to a method of kinetic resolution represented by Scheme 2:

Scheme 2

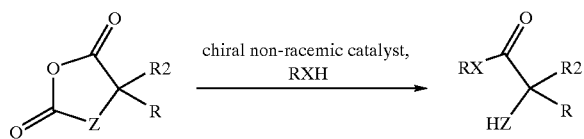

wherein

X represents NR', O, or S;

Z represents NR', O, or S;

R and R2 represent independently for each occurrence hydrogen, or optionally substituted alkyl, aryl, heteroaryl, aralkyl, or heteroaralkyl; provided that R and R2 are not the same;

R' represents independently for each occurrence R, formyl, acyl, sulfonyl, —$CO_2R$, or —$C(O)NR_2$;

chiral non-racemic catalyst is a chiral non-racemic tertiary amine, phosphine, or arsine; and when said method is completed or interrupted, the enantiomeric excess or diastereomeric excess of the unreacted substrate is greater than that of the substrate prior to the kinetic resolution, the enantiomeric excess or diastereomeric excess of the product is greater than zero, or both.

In certain embodiments, the kinetic resolution method of the present invention is represented by Scheme 2 and the attendant definitions, wherein X represents O.

In certain embodiments, the kinetic resolution method of the present invention is represented by Scheme 2 and the attendant definitions, wherein Z represents NR' or O.

In certain embodiments, the kinetic resolution method of the present invention is represented by Scheme 2 and the attendant definitions, wherein said chiral non-racemic catalyst is a chiral non-racemic tertiary amine.

In certain embodiments, the kinetic resolution method of the present invention is represented by Scheme 2 and the attendant definitions, wherein said chiral non-racemic catalyst is a cinchona alkaloid.

In certain embodiments, the kinetic resolution method of the present invention is represented by Scheme 2 and the attendant definitions, wherein said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

In certain embodiments, the kinetic resolution method of the present invention is represented by Scheme 2 and the attendant definitions, wherein X represents O; and Z represents NR' or O.

In certain embodiments, the kinetic resolution method of the present invention is represented by Scheme 2 and the attendant definitions, wherein X represents O; Z represents NR' or O; and said chiral non-racemic catalyst is a chiral non-racemic tertiary amine.

In certain embodiments, the kinetic resolution method of the present invention is represented by Scheme 2 and the attendant definitions, wherein X represents O; Z represents NR' or O; and said chiral non-racemic catalyst is a cinchona alkaloid.

In certain embodiments, the kinetic resolution method of the present invention is represented by Scheme 2 and the attendant definitions, wherein X represents O; Z represents NR' or O; and said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

In certain embodiments, the kinetic resolution method of the present invention is represented by Scheme 2 and the attendant definitions, wherein the enantiomeric or diastereomeric excess of the product or unreacted substrate is greater than about 50%.

In certain embodiments, the kinetic resolution method of the present invention is represented by Scheme 2 and the attendant definitions, wherein the enantiomeric or diastereomeric excess of the product or unreacted substrate is greater than about 70%.

In certain embodiments, the kinetic resolution method of the present invention is represented by Scheme 2 and the attendant definitions, wherein the enantiomeric or diastereomeric excess of the product or unreacted substrate is greater than about 90%.

Nucleophiles

Nucleophiles useful in the present invention may be determined by the skilled artisan according to several criteria. In general, a suitable nucleophile will have one or more of the following properties: 1) It will be capable of reaction with the substrate at the desired electrophilic site; 2) It will yield a useful product upon reaction with the substrate; 3) It will not react with the substrate at functionalities other than the desired electrophilic site; 4) It will react with the substrate at least partly through a mechanism catalyzed by the chiral catalyst; 5) It will not substantially undergo further undesired reaction after reacting with the substrate in the desired sense; and 6) It will not substantially react with or degrade the catalyst. It will be understood that while undesirable side reactions (such as catalyst degradation) may occur, the rates of such reactions can be rendered slow—through the selection of appropriate reactants and conditions—in comparison with the rate of the desired reaction(s).

Nucleophiles which satisfy the above criteria can be chosen for each substrate and will vary according to the substrate structure and the desired product. Routine experimentation may be necessary to determine the preferred nucleophile for a given transformation. For example, if a nitrogen-containing nucleophile is desired, it may be selected from ammonia, phthalimide, hydrazine, an amine or the like. Similarly, oxygen nucleophiles such as water, hydroxide, alcohols, alkoxides, siloxanes, carboxylates, or peroxides may be used to introduce oxygen; and mercaptans, thiolates, bisulfite, thiocyanate and the like may be used to introduce a sulfur-containing moiety. Additional nucleophiles will be apparent to those of ordinary skill in the art.

For anionic nucleophiles, the counterion can be any of a variety of conventional cations, including alkali metal cations, alkaline earth cations, and ammonium cations.

In certain embodiments, the nucleophile may be part of the substrate, thus resulting in an intramolecular reaction.

Substrates

As discussed above, a wide variety of racemic and diastereomeric mixtures serve as substrates in the methods of the present invention. The choice of substrate will depend on factors such as the nucleophile to be employed and the desired product, and an appropriate substrate will be apparent to the skilled artisan. It will be understood that the substrate preferably will not contain any functionalities that interfere with kinetc resolution of the present invention. In general, an appropriate substrate will contain at least one reactive electrophilic moiety at which a nucleophile may attack with the assistance of the catalyst. The catalyzed, stereoselective transformation of one enantiomer of a racemic mixture, or one diastereomer of a distereomeric mixture, is the basis of the kinetic resolutions of the present invention.

Most of the substrates contemplated for use in the methods of the present invention contain at least one ring having three to seven atoms. Small rings are frequently strained, enhancing their reactivity. However, in some embodiments a cyclic substrate may not be strained, and may have a larger electrophilic ring.

Examples of suitable cyclic substrates in the subject methods include compounds 1–6, depicted below. In certain embodiments, the substrate will be a racemic mixture. In certain embodiments, the substrate will be a mixture of diastereomers.

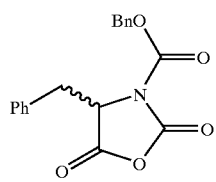

1

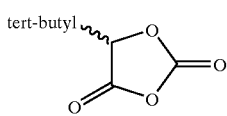

2

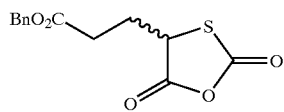

3

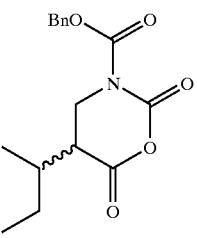

4

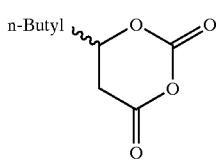

5

-continued

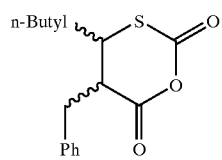

6

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions that will not adversely effect the substrate, the catalyst, or the product. For example, the reaction temperature influences the speed of the reaction, as well as the stability of the reactants, products, and catalyst. The reactions will usually be run at temperatures in the range of −78° C. to 100° C., more preferably in the range −20° C. to 50° C. and still more preferably in the range −20° C. to 25° C.

In general, the asymmetric synthesis reactions of the present invention are carried out in a liquid reaction medium. The reactions may be run without addition of solvent, e.g., where the nucleophile is a liquid. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent that is not inert to the substrate under the conditions employed, e.g., use of ethanol as a solvent when ethanol is the desired nucleophile. In embodiments where water and hydroxide are not preferred nucleophiles, the reactions can be conducted under anhydrous conditions. In certain embodiments, ethereal solvents are preferred. In embodiments where water and hydroxide are preferred nucleophiles, the reactions are run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. For example, kinetic resolutions with cyanide as nucleophile may be performed under an atmosphere of HCN gas. The partial pressure of the reactive gas may be from 0.1 to 1000 atmospheres, more preferably from 0.5 to 100 atm, and most preferably from about 1 to about 10 atm.

In certain embodiments it is preferable to perform the reactions under an inert atmosphere of a gas such as nitrogen or argon.

The asymmetric synthesis methods of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation.

Exemplification

The invention now being generally described, it will be more readily understood by reference to the following examples that are included merely for purposes of illustration of certain aspects and embodiments of the present invention, and are not intended to limit the invention.

EXAMPLE 1
Dynamic Kinetic Resolution of 5-Phenyl-1,3-dioxolane-2,4-dione Using (DHQD)$_2$AQN -continued

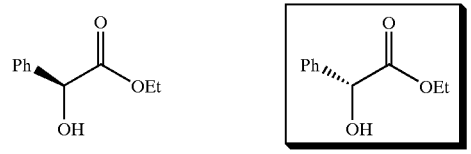

A solution of 5-phenyl-1,3-dioxolane-2,4-dione (17.8 mg, 0.1 mmol) and (DHQD)$_2$AQN (18.2 mg, 0.02 mmol) in anhydrous diethyl ether (4 mL) was treated with absolute EtOH (9 µL) at −78° C. The resulting reaction mixture was stirred for 8 hours at this temperature. The reaction was then quenched with HCl (0.2 N, 5 mL). The organic phase was separated, and the aqueous phase was extracted with diethyl ether (2×2.0 mL). The combined organic layers were dried over anhydrous sodium sulfate and concentrated in vacuo. The residue was purified by column chromatography (silica gel, Hexane/Ethyl Acetate=2:1) to afford the mandelic ethyl ester as a colorless oil (12 mg, 67% yield). The enantiomeric excess of the mandelic ethyl ester was determined to be 97% by chiral HPLC analysis.

EXAMPLE 2
Dynamic Kinetic Resolution of 5-Phenyl-1,3-dioxolane-2,4-dione Using Quinidine

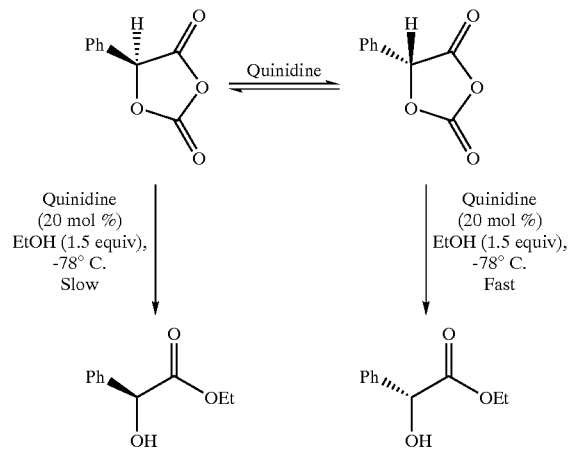

A solution of 5-phenyl-1,3-dioxolane-2,4-dione (17.8 mg, 0.1 mmol) and quinidine (6.5 mg, 0.02 mmol, 97% pure) with 10 mg dry 4 angstrom molecule sieves was treated with EtOH (9 µL) in one portion at −78° C., then the reaction mixture was stirred for 8 hours at this temperature. The reaction was quenched with a large excess of methanol. The conversion was determined to be 52% by GC. The enantiomeric excess of the product was determined to be 85% via chiral HPLC.

EXAMPLE 3
Kinetic Resolution of Racemic 5-Benzyl-1-aza-3-oxolane-2,4-dione Using (DHOD)$_2$AQN

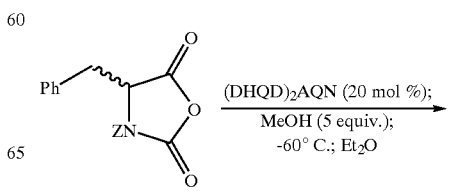

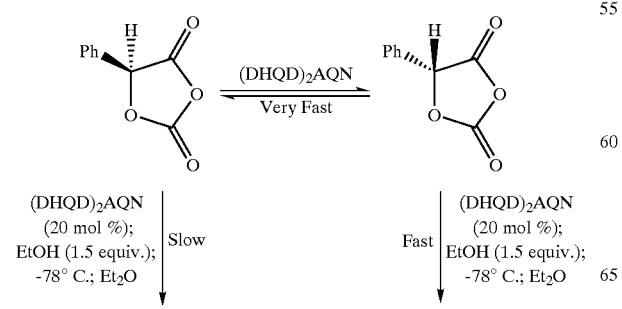

-continued

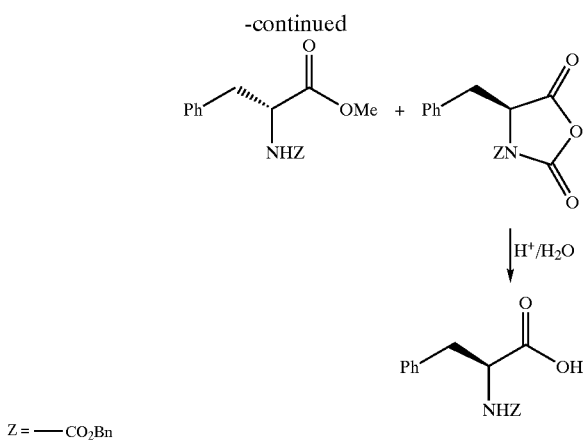

Z = —CO₂Bn

To a solution of racemic Phenylalanine UNCA(15.3 mg, 0.047 mmol) and (DHQD)₂AQN (7.7 mg, 0.009 mmol) in dry diethyl ether (3.5 mL) at −60° C. was added dry methanol (0.25 mmol) in one portion. The resulting clear solution was stirred at −60° C. for 5.5 hours. The reaction mixture was quenched with HCl (2 N, 2.0 mL). The organic phase was separated, and the aqueous phase was extracted with ether (2×1.0 mL). The combined organic layers were washed with HCl (2 N, 2×1.0 mL), followed by NaOH (2 N, 1×3.0 mL), dried over anhydrous Na₂SO₄, and concentrated in vacuo to give the amino ester as a colorless oil (7.0 mg, 47% yield). The basic aqueous phase was acidified to pH<3 with concentrated HCl, and extracted with ether (2×10 mL). The combined organics were dried over anhydrous Na₂SO₄, and concentrated in vacuo to give the amino acid (5.2 mg, 37% yield). The enantiomeric excess of the amino ester and the amino acid were determined to be 93% and 94%, respectively, by HPLC analysis.

EXAMPLE 4
Kinetic Resolution of Racemic 5-Benzyl-1-aza-3-oxolane-2,4-dione Using Quinidine

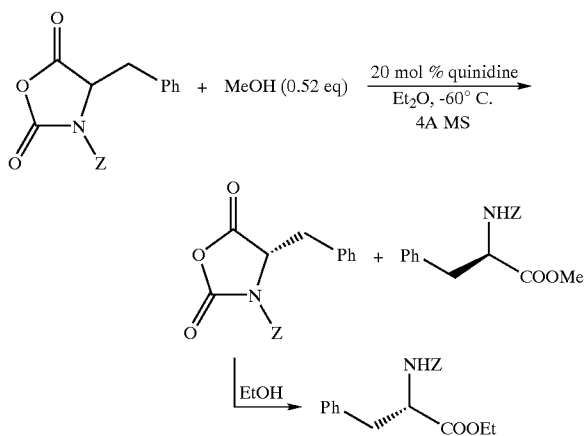

To a mixture of UNCA(Phe-Z) (16.3 mg, 0.05 mmol), (+)-quinidine (3.2 mg, 0.01 mmol) and 4A molecular sieves (10 mg), anhydrous ether (3.5 mL) was added, the resulting mixture was stirred at room temperature for 15 minutes, then cooled to −60° C. and methanol solution in ether (5% v/v), 21.1 μL, 0.026 mmol of methanol) was introduced. The resulting reaction mixture was stirred at −60° C. for 40 h. A small amount of reaction mixture (50 μL) was added to dry ethanol (200 μL) and the resulting solution was stirred at room temperature for 30 min., then passed through a silica gel plug with ether as the eluent. The solvent was removed under reduced pressure to give a mixture of methyl and ethyl esters for GC (HP-5 column, 200° C., 4 min., raised to 250° C. at 10° C./min and 250° C., 8 min) and chiral HPLC (Daicel chiralpak OJ column, 4:1, Hexanes:IPA, 0.7 mL/min, λ=220 nm) analysis. The conversion of the starting material was 43.8%, the enantiomeric excess of the product was 85.6%, and the enantiomeric excess of the starting material was 69.2%, as reflected by the ethyl ester. Based on these numbers, the selective factor (s=$k_{fast}$, $k_{slow}$) was calculated to be larger than 20.

EXAMPLE 5
General Procedure for the Preparation of Dioxolanediones

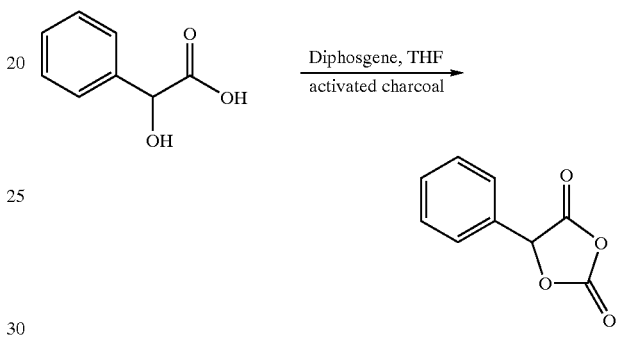

Mandelic acid (0.5 g) was dissolved in 5 mL dry THF, and treated with diphosgene (0.8 ml), then added catalytic amount of activated charcoal (about 10 mg). The mixture was stirred at room temperature overnight, and filtered through Celite. The solvent was removed under vacuum to give the product in roughly quantitative yield (>95%).

EXAMPLE 6
Preparation of α-Amino Acid N-Carboxy Anhydrides (NCAs and UNCAs)
General Procedures
A. NCAs

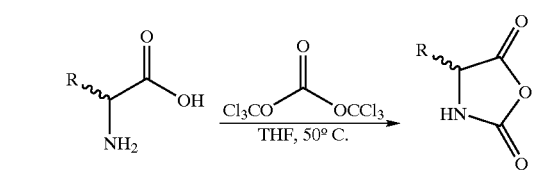

To a suspension of the racemic acid (3.0–25.0 mmol) in anhydrous THEF (8–40 mL) at 50° C. was added triphosgene (1.0 eq.) in one portion. If a clear solution has not formed within one hour, 1–2 aliqouts of triphosgene (0.1 eq/aliquot) were added to the reaction mixture at 45 min intervals. The reaction mixture was stirred at 50° C. for a total of 3 h, afterwhich the insoluble material (if there is any) in the reaction mixture was removed by filtration. The filtrate was poured into hexanes (20–120 mL) and the resulting mixture was stored in a freezer (−20° C.) overnight. The white crystals formed during this time were collected and dried under vacuum to give the desired NCAs, which were used for the next step without further purification.

B. UNCAs

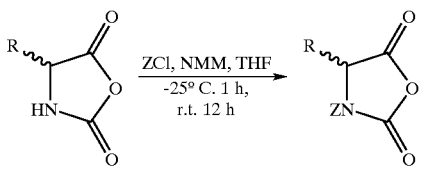

To a solution of the racemic NCA (1.0–10.0 mmol) in dry THF (5.0–25.0 mL) at −25° C., alkyl (benzyl, allyl and fluorenylmethyl) chloroformate (1.2–1.3 eq.) was added. A solution of N-methyl-morpholine (NMM) (1.25–1.5 eq.) in THF (1.0–5.0 mL) was introduced dropwise to the reaction mixture over a period of 15 min. The resulting mixture was stirred at −25° C. for 1 h, then allowed to warm to room temperature overnight. The reaction mixture was cooled to −25° C. and acidified by HCl (4.0 M in Dioxane) until the pH of the mixture is approximately 3. The resulting mixture was allowed to warm to room temperature. The precipitation (NMM hydrochloride) was removed by filtration under $N_2$ atmosphere with the aid of dry Celite 521 (3.0 g) and washed with dry THF (2×20 mL). The filtrate was concentrated and the residue was subjected to recrystallization from TBME/THF/hexanes at −20° C. overnight. The white solid was collected and dried under vacuum to give the desired UNCAs in yields ranging from 47 to 86% (average yield for 14 UNCAs listed in Table 3 is 67%) from racemic amino acid.

Specific Compounds Prepared

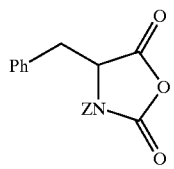

2a

This product was obtained in 72% yield from the corresponding racemic amino acid. m.p. 105–106° C.; $^1$H NMR (400 MHz, CDCl$_3$) δ 3.28 (dd, J=14.0 and 2.4 Hz, 1H), 3.47 (dd, J=14.0 and 5.5 Hz, 1H), 4.93 (dd, J=5.5 and 2.4 Hz, 1H), 5.40 (s, 1H), 6.88–6.90 (m, 2H), 7.21–7.26 (m, 3H), 7.41–7.47 (m, 5H); $^{13}$C NMR (100 MHz, CDCl$_3$) δ 35.06, 60.98, 69.77, 128.22, 128.71, 128.83, 129.10, 129.13, 129.35, 131.92, 134.10, 145.52, 149.18, 165.37.

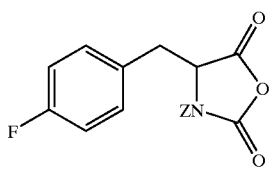

2b

This product was obtained in 79% yield from the corresponding racemic amino acid. $^1$H NMR (400 MHz, CDCl$_3$) δ 3.23–3.30 (m, 1H), 3.41–3.49 (m, 1H), 4.89–4.96 (m, 1H), 5.04 (s, 2H), 6.81–6.93 (m, 4H), 7.41–7.48 (m, 5H); $^{13}$C NMR (100 MHz, CDCl$_3$) δ 34.45, 61.09, 70.10, 116.36 (d, J=21.2 Hz), 127.91, 129.01, 129.07, 129.40, 131.30, 134.27, 145.64, 149.41, 161.73 (d, J=246 Hz), 165.50; IR (CHCl$_3$) γ 1874, 1809, 1743, 1511, 1456 cm$^{-1}$; HRMS (DCI) exact mass calcd for (C$_{18}$H$_{14}$NO$_5$F+NH$_4^+$) requires m/z 361.1200, found m/z 361.1212.

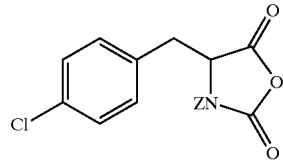

2c

This product was obtained in 47% yield from the corresponding racemic amino acid. $^1$H NMR (400 MHz, CDCl$_3$) δ 3.26 (dd, J=14.3 and 2.2 Hz, 1H), 3.44 (dd, J=14.3 and 5.8 Hz, 1H), 4.93 (dd, J=2.2 and 5.8 Hz, 1H), 5.40 (s, 1H), 6.81 (d, J=8.5 Hz, 2H), 7.17 (d, J=8.5 Hz, 2H), 7.40–7.50 (m, 5H); $^{13}$C NMR (100 MHz, CDCl$_3$) δ 34.37, 60.69, 69.90, 128.79, 128.86, 129.20, 129.34, 130.44, 130.69, 134.01, 134.31, 145.37, 149.17, 165.18; IR (CHCl$_3$) γ 1874, 1809, 1743, 1493, 1456, 1362, 1264, 1015, 960 cm$^{-1}$; HRMS (DCI) exact mass calcd for (C$_{18}$H$_{14}$ClNO$_5$+NH$_4^+$) requires m/z 377.0904, found m/z 377.0921.

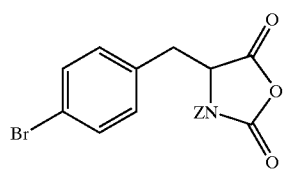

2d

This product was obtained in 77% yield from the corresponding racemic amino acid. $^1$H NMR (400 MHz, CDCl$_3$) δ 3.20–3.26 (m, 1H), 3.37–3.45 (m, 1H), 4.88–4.95 (m, 1H), 5.39 (s, 2H), 6.74 (d, J=8.2 Hz, 2H), 7.32 (d, J=8.2 Hz, 2H), 7.39–7.47 (m, 5H); $^{13}$C NMR (100 MHz, CDCl$_3$) δ 34.66, 60.87, 70.15, 122.63, 128.99, 129.06, 129.39, 131.21, 132.48, 134.20, 145.59, 149.33, 165.38; IR (CHCl$_3$) γ 1873, 1809, 1744, 1489, 1456 cm$^{-1}$; HRMS (DCI) exact mass calcd for (C$_{18}$H$_{14}$NO$_5$Br+NH$_4^+$) requires m/z 421.0399, found m/z 421.0386.

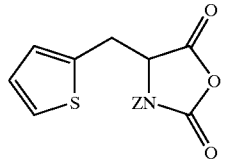

2e

This product was obtained in 62% yield from the corresponding racemic amino acid. $^1$H NMR (400 MHz, CDCl$_3$) δ 3.52–3.57 (m, 1H), 3.73–3.78 (m, 1H), 4.91–4.93 (m, 1H), 5.40 (d, J=12.0 Hz, 1H), 5.44 (d, J=12.0 Hz, 1H), 6.68–6.69 (m, 1H), 6.90–6.92 (m, 1H), 7.19–7.20 (m, 1H), 7.38–7.49 (m, 5H); $^{13}$C NMR (100 MHz, CDCl$_3$) δ 29.43, 60.93, 69.91, 126.29, 127.71, 128.12, 128.73, 128.90, 129.12, 132.83, 134.17, 145.83, 149.10, 165.41; IR (CHCl$_3$) γ 1874, 1808, 1739, 1519, 1456 cm$^{-1}$; HRMS (DCI) exact mass calcd for (C$_{16}$H$_{13}$NO$_5$S+NH$_4^+$) requires m/z 349.0858, found m/z 349.0844.

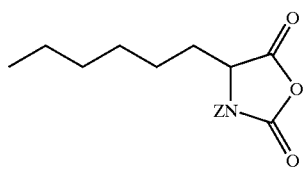

2f

This product was obtained in 54% yield from the corresponding racemic amino acid. $^1$H NMR (400 MHz, CDCl$_3$) δ 0.84 (t, J=7.0 Hz, 3H), 1.15–1.36 (m, 8H), 1.95–2.18 (m, 2H), 4.71 (dd, J=6.7 and 3.1 Hz, 1H), 5.29 (d, J=11.9 Hz, 1H), 5.38 (d, J=11.9 Hz, 1H), 7.30–7.42 (m, 5H); $^{13}$C NMR (100 MHz, CDCl$_3$) δ 13.89, 22.33, 23.01, 28.44, 29.72, 31.22, 59.94, 69.64, 128.39, 128.77, 128.96, 134.02, 146.21, 148.97, 165.88; IR (CHCl$_3$) γ 2930, 2858, 1871, 1812, 1742, 1498, 1456, 1387, 1304 cm$^{-1}$; HRMS (DCI) exact mass calcd for (C$_{17}$H$_{21}$NO$_5$+NH$_4^+$) requires m/z 337.1763, found m/z 337.1758.

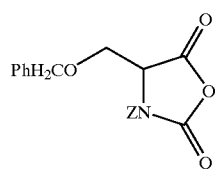

2g

This product was obtained in 61% yield from the corresponding racemic amino acid. $^1$H NMR (400 MHz, CDCl$_3$) δ 3.83–3.89 (m, 1H), 3.97–4.03 (m, 1H), 4.44 (d, J=12.4 Hz, 1H), 4.51 (d, J=12.4 Hz, 1H), 4.64–4.70 (m, 1H), 5.25 (s, 2H), 7.17–7.22 (m, 2H), 7.27–7.39 (m, 8H); $^{13}$C NMR (100 MHz, CDCl$_3$) δ 61.14, 65.47, 69.81, 73.59, 127.87, 128.35, 128.54, 128.78, 128.98, 129.13, 134.20, 136.72, 146.36, 149.10, 164.73; IR (CHCl$_3$) γ 1876 1808, 1745, 1496, 1454 cm$^{-1}$; HRMS (DCI) exact mass calcd for (C$_{19}$H$_{17}$NO$_6$+NH$_4^+$) requires m/z 373.1400, found m/z 373.1409.

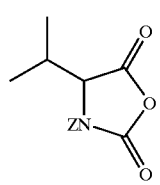

2h

This product was obtained in 84% yield from the corresponding racemic amino acid. m.p. 79–81° C.; $^1$H NMR (400 MHz, CDCl$_3$) δ 0.95 (d, J=7.3 Hz, 3H), 1.20 (d, J=7.3 Hz, 3H), 2.50–2.62 (m, 1H), 4.61 (d, J=3.7 Hz, 1H), 5.34 (d, J=12.2 Hz, 1H), 5.38 (d, J=12.2 Hz, 1H), 7.30–7.48 (m, 5H); $^{13}$C NMR (100 MHz, CDCl$_3$) δ 15.75, 17.92, 29.94, 64.98, 69.96, 128.51, 129.02, 129.04, 129.18, 134.25, 146.50, 149.44, 164.48.

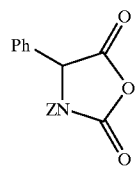

2i

This product was obtained in 60% yield from the corresponding racemic amino acid. $^1$H NMR (400 MHz, CDCl$_3$) δ 5.16 (d, J=11.9 Hz, 1H), 5.25 (d, J=11.9 Hz, 1H), 5.62 (s, 1H), 7.14–7.18 (m, 2H), 7.24–7.46 (m, 8H); $^{13}$C NMR (100 MHz, CDCl$_3$) δ 63.38, 69.80, 126.55, 128.30, 128.64, 128.86, 129.52, 130.06, 131.48, 133.71, 146.10, 148.39, 163.73; IR (CHCl$_3$) γ 1874, 1812, 1746, 1498, 1456, 1354, 1242, 1008 cm$^{-1}$; HRMS (DCI) exact mass calcd for (C$_{17}$H$_{13}$NO$_5$+NH$_4^+$) requires m/z 329.1137, found m/z 329.1125.

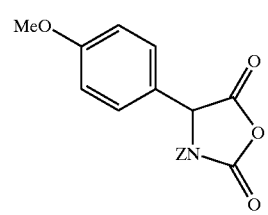

2j

This product was obtained in 86% yield from the corresponding racemic amino acid. $^1$H NMR (400 MHz, CDCl$_3$) δ 3.81 (s, 3H), 5.14 (d, J=12.0 Hz, 1H), 5.23 (d, J=12.0 Hz, 1H), 5.55 (s, 1H), 6.87–6.90 (m, 2H), 7.14–7.22 (m, 4H), 7.27–7.32 (m, 3H); $^{13}$C NMR (100 MHz, CDCl$_3$) δ 55.58, 63.20, 69.83, 115.02, 123.65, 128.37, 128.49, 128.78, 128.97, 134.02, 146.43, 148.65, 160.97, 164.46; IR (CHCl$_3$) γ 1873, 1814, 1749, 1611, 1586, 1515, 1455 cm$^{-1}$; HRMS (DCI) exact mass calcd for (C$_{18}$H$_{15}$NO$_6$+NH$_4^+$) requires m/z 359.1243, found m/z 359.1227.

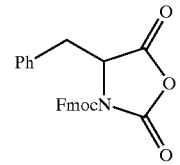

2k

This product was obtained in 73% yield from the corresponding racemic amino acid. $^1$H NMR (400 MHz, CDCl$_3$) δ 3.00–3.16 (m, 2H), 4.34 (t, J=6.1 Hz, 1H), 4.68 (dd, J=5.5 and 3.1 Hz, 1H), 4.72–4.84 (m, 2H), 6.80–6.90 (m, 2H), 7.20–7.32 (m, 3H), 7.32–7.40 (m, 2H), 7.40–7.40 (m, 2H), 7.64 (d, J=7.3 Hz, 1H), 7.70 (d, J=7.3 Hz, 1H), 7.74–7.84 (m, 2H); $^{13}$C NMR (100 MHz, CDCl$_3$) δ 34.74, 46.47, 60.87, 69.56, 120.16, 120.23, 124.91, 124.98, 127.42, 127.49, 128.18, 128.23, 129.12, 129.34, 131.85, 141.33, 141.39, 142.71, 142.77, 145.54, 149.05, 165.25.

21

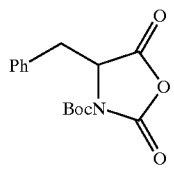

D,L-phenylalanine NCA (1.615 g, 8.45 mmol) was dissolved in THF (23 mL). The solution was then cooled to −15° C. with stirring and Boc$_2$O (2.40 g, 11.0 mmol), pyridine (1.38 mL, 17.0 mmol) and flamed-dried powdered 4A molecular sieves (0.2 g) were added successively. The flask was sealed and stored in a freezer at −15° C. for 6 days. For other procedure, see the typical prodedure. This product was obtained in 63% yield from the corresponding racemic amino acid. m.p. 101–103° C.; $^1$H NMR (400 MHz, CDCl$_3$) δ 1.62 (s, 9H), 3.33 (dd, J=14.3 and 2.5 Hz, 1H), 3.52 (dd, 14.3 and 5.6 Hz, 1H), 4.91 (dd, J=5.6 and 2.5 Hz, 1H), 7.05–7.12 (m, 2H), 7.29–7.37 (m, 3H); $^{13}$C NMR (100 MHz, CDCl$_3$) δ 27.92, 35.27, 60.75, 86.02, 128.24, 129.13, 129.43, 132.26, 145.76, 147.62, 165.78.

2m

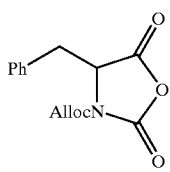

This product was obtained in 61% yield from the corresponding racemic amino acid. $^1$H NMR (400 MHz, CDCl$_3$) δ 3.35 (dd, J=14.2 and 2.4 Hz, 1H), 3.55 (dd, 14.2 and 5.6 Hz, 1H), 4.83–4.92 (m, 2H), 4.98 (dd, 5.6 and 2.4 Hz, 1H), 5.37–5.55 (m, 2H), 5.95–6.06 (m, 1H), 7.00–7.12 (m, 2H), 7.22–7.40 (m, 3H); $^{13}$C NMR (100 MHz, CDCl$_3$) δ 35.16, 60.93, 68.66, 120.51, 128.34, 129.21, 129.44, 130.24, 132.02, 145.51, 149.16, 165.34; IR (CHCl$_3$) γ 3032, 1872, 1808, 1743, 1497, 1455, 1374, 1266 cm$^{-1}$; HRMS (DCI) exact mass calcd for (C$_{14}$H$_{13}$NO$_5$+NH$_4^+$) requires m/z 293.1137, found m/z 193.1147.

2n

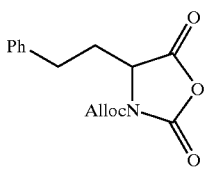

This product was obtained in 64% yield from the corresponding racemic amino acid. 1H NMR (400 MHz, CDCl$_3$) δ 2.42–2.55 (m, 2H), 2.67–2.84 (m, 2H), 4.70–4.82 (m, 3H), 5.32–5.40 (m, 1H), 5.40–5.50 (m, 1H), 7.14–7.38 (m, 5H); $^{13}$C NMR (100 MHz, CDCl$_3$) δ 29.74, 30.98, 59.31, 68.62, 120.63, 126.79, 128.32, 128.77, 130.16, 138.67, 145.91, 148.87, 165.63; IR (CHCl$_3$) γ 3028, 2940, 1870, 1808, 1743, 1497, 1455, 1376, 1307 cm$^{-1}$.

EXAMPLE 7

General Method for the Kinetic Resolution of Urethane-Protected α-Amino Acid N-Carboxy Anhydrides (UNCAs)

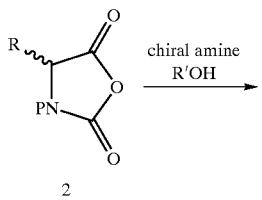

2

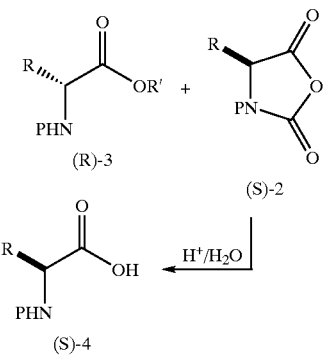

P: -Z
-Boc
-Alloc
-Fmoc

A mixture of an UNCA 2 (0.10 mmol) and 4 Å molecular sieves (10 mg) in anhydrous diethyl ether (7.0 mL) was stirred at room temperature for 15 minutes, then cooled to the temperature indicated in Table 3, afterwhich the modified cinchona alkaloid (0.01 mmol) was added to the mixture. The resulting mixture was stirred for another 5 minutes and then a solution of methanol in ether (v/v=1/19, 0.052–0.10 mmol of methanol, in entry 9 and 10, 0.055 mmol of ethanol was used) was introduced dropwise via a syringe. The resulting reaction mixture was stirred at that temperature for 15–85 h. The reaction was quenched by HCl in ether (1 N, 1.0 mL). After 15 minutes, aq. HCl (2 N, 2.0 mL) was added to the reaction mixture, and the resulting mixture was allowed to warm to room temperature. The organic phase was collected, washed with aq.HCl (2 N, 2×1 mL), dried (NaSO$_4$), and concentrated. The residue was dissolved in H$_2$O/THF (v/v: 1/4, 5.0 mL) and the resulting solution was stirred at room temperature overnight. The solution was then concentrated and the residue was dissolved in ether (3.0 mL). The resulting resolution was extracted with aq. Na$_2$CO$_3$ (1 N, 2×3.0 mL). The organic layer was washed with water (1.0 mL), dried (Na$_2$SO$_4$), and concentrated to give amino esters 3 in NMR-pure form and in yields indicated in Table 3. The aqueous phases were combined and then acidified with conc. HCl till pH<3, then extracted with ethyl acetate (3×10 mL). The organic phase was dried (Na$_2$SO$_4$), and concentrated to give amino acids 4 in NMR-pure form and in yields indicated in Table 3. This procedure described above is used for the kinetic resolution of 2a–d, f–i, k–n.

For kinetic resolutions of 2e and 2j, chromatographic purification was used for the isolation of amino esters 3e, 3j and amino acids 4e, 4j as following: After the reaction was quenched and the catalyst was converted to the corresponding ammonium salt with aq. HCl as described above, the residue obtained from concentration of the organic phase (instead of being subjected to exhaustive hydrolysis in H₂O/THF) was subjected to flash chromatography (SiO₂) with first ether/hexanes (v/v=1/5) as eluent to give the desired esters 3 (e, j) and then ether/AcOH (v/v=100/1) as eluent to give the desired amino acids 4 (e, j) in NMR-pure form and in yields indicated in Table 3.

EXAMPLE 8
General Method for Determining the Extent of Conversion of a Kinetic Resolution of Urethane-Protected α-Amino Acid N-Carboxy Anhydrides (UNCAs)

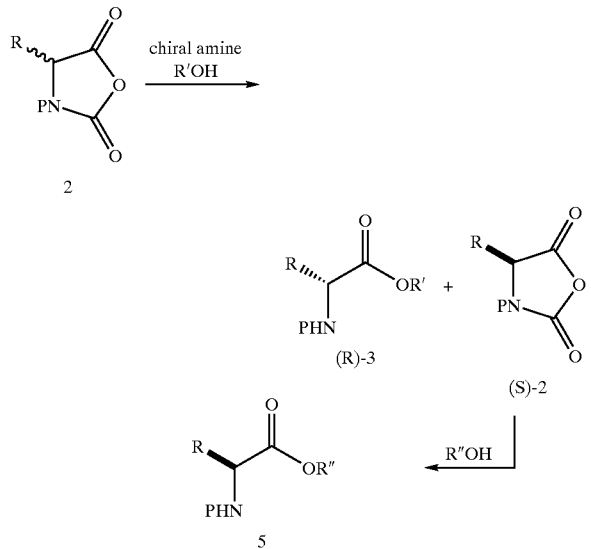

When R'OH = MeOH, R"OH = EtOH
R'OH = EtOH, R"OH = MeOH

P: -Z
 -Boc
 -Alloc
 -Fmoc

A small aliquot (50 μL) of a reaction mixture was added to dry ethanol (200 μL). The resulting mixture was stirred at r.t. for 30min, then was allow to pass through a plug of silica gel with ether. The solution was concentrated and then subjected to GC analysis (HP-5 column, 200° C., 4 min., 10° C./min to 250° C., 250° C., 8–12 min). For kinetic resolutions of UNCA 2i and 2j using ethanol as the nucleophile (entries 9 and 10, Table 3), the aliquot of the reaction mixture was added to dry methanol. The experimentally-determined conversions and the calculated conversions, as indicated below, are consistent with each other.

EXAMPLE 9
General Procedure for Determining the Enantiomeric Excesses of the Products and Unreacted Starting Materials of the Kinetic Resolutions The enantiomeric excesses of esters 3 were determined by HPLC analyses following conditions specified below. The enantiomeric excesses of the unreacted UNCAs 2 were determined by converting 2 to esters 5 as described above and measuring enantiomeric excesses of ester 5 by HPLC analyses following conditions specified below. The enantiomeric excesses of amino acids 4 were determined by HPLC analyses and were found to be, without exception, consistent with the enantiomeric excesses of the corresponding esters 5.

(S)-(N-Benzyloxycarbonyl)phenylalanine (4a)

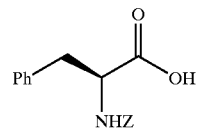

In a large scale (4 mmol) reaction, this product was obtained as a white solid in 48% isolated yield and 97% ee (as a ethyl ester) as determined by chiral HPLC analysis [Daicel chiralpak OJ column, Hexanes:IPA, 80:20, 0.7 mL/min, λ 220 nm, t(major, ethyl ester)=18.47 min, t(minor, ethyl ester)=21.42 min], m.p. $[α]_D$=+4.8 (c 2.21, AcOH); (Literature, $[α]_D$=+5.1 (c 2.0, AcOH), for S-enantiomer); ¹H NMR (400 MHz, CDCl₃, 4.7:1 mixture of rotamers) δ 3.02–3.24 (m, 2H), 3.62–3.74 (m, 1H), 5.10 (s, 2H), 5.17 (d, J=7.9 Hz, 1H), 7.10–7.38 (m, 10H); ¹H NMR (minor rotamer, partial) δ 2.92–3.04 (m, 2H), 4.50–4.60 (m, 1H), 4.90–5.04 (m, 2H), 5.70–5.80 (m, 1H); ¹³C NMR (100 MHz, CDCl₃) δ 37.70, 54.52, 67.16, 127.28, 128.11, 128.26, 128.54, 128.71, 129.31, 135.38, 136.02, 155.84, 175.89.

(R)-Methyl-(N-Benzyloxycarbonyl)phenylalaninate (3a)

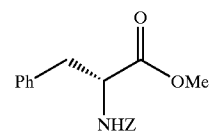

This product was obtained as a colorless oil in 48% isolated yield and 93% ee as determined by chiral HPLC analysis [Daicel chiralpak OJ column, Hexanes:IPA, 80:20, 0.7 mL/min, λ 220 nm, t(minor)=24.78 min, t(major)=37.56 min]. $[α]_D$=+13.9 (c 1.60, MeOH); (Literature, $[α]_D^{19}$=−15.6 (c 1.02, MeOH), for S-enantiomer); ¹H NMR (400 MHz, CDCl₃, 5.5:1 mixture of rotamers) δ 3.02–3.18 (m, 2H), 3.72 (s, 3H), 4.68 (dd, J=14.0 and 6.1 Hz, 1H), 5.02–5.14 (m, 2H), 5.21 (br d, J=7.9 Hz, 1H), 7.02–7.14 (m, 2H), 7.20–7.40 (m, 8H); ¹H NMR (minor rotamer, partial) δ 2.92–3.04 (m, 2H), 3.66 (s, 3H), 4.48–4.58 (m, 1H), 4.92–5.02 (m, 2H); ¹³C NMR (100 MHz, CDCl₃) δ 38.22, 52.28, 54.78, 66.95, 127.13, 128.06, 128.17, 128.50, 128.59, 129.24, 135.66, 136.24, 155.60, 171.94.

Ethyl (N-Benzyloxycarbonyl)phenylalaninate (5a):

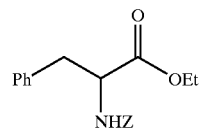

¹H NMR (400 MHz, CDCl₃, 5.6:1 mixture of rotamers) δ 1.22 (t, J=7.3 Hz, 3H), 3.04–3.18 (m, 2H), 4.16 (q, J=7.3 Hz, 2H), 4.64 (dd, J=14.0 and 6.1 Hz, 1H), 5.10 (s, 2H), 5.25 (d, J=7.9 Hz, 1H), 7.06–7.14 (m, 2H), 7.18–7.40 (m, 8H); ¹H NMR (minor rotamer, partial) δ 2.92–3.04 (m, 1H), 4.46–4.56 (m, 1H), 4.98–5.06 (m, 2H); ¹³C NMR (100 MHz, CDCl₃) δ 14.05, 38.27, 54.81, 61.46, 66.90, 127.06, 128.05, 128.14, 128.49, 128.52, 129.31, 135.74, 136.26, 155.58, 171.46.

(S)-(N-Benzyloxycarbonyl)-p-fluorophenylalanine (4b)

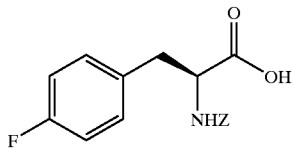

This product was obtained as a white solid in 42% isolated yield and 92% ee (as a ethyl ester) as determined by chiral HPLC analysis [Daicel chiralpak OD column, Hexanes:IPA, 95:5, 1.0 mL/min, λ220 nm, t(minor, ethyl ester)=25.98 min, t(major, ethyl ester)=17.47 min] from a reaction catalyzed by $(DHQD)_2AQN$ (10 mol %). This reaction employed 0.55 eq. of methanol and was stirred at −78° C. for 31 h when the reaction conversion reached 50%. $[\alpha]_D$=+(c 0.92, EtOH); $^1$H NMR (400 MHz, $CDC_3$, 3.0:1 mixture of rotamers) δ 3.00–3.08 (m, 1H), 3.10–3.21 (m, 1B), 4.62–4.70 (m, 1H), 5.06 (d, J=12.0 Hz, 1H), 5.12 (d, J=12.0 Hz, 1H), 5.23–5.28 (m, 1H), 6.90–6.99 (m, 2H), 7.01–7.12 (m, 2H), 7.28–7.39 (m, 5H), 8.60 (s, br., 1H); $^1$H NMR (minor rotamer, partial) δ 2.85–2.94 (m, 1H), 3.04–3.14 (m, 1H), 4.44–4.52 (m, 1H), 6.26–6.32 (m, 1H); $^{13}$C NMR (100 MHz, $CDCl_3$) δ 37.18, 54.85, 67.43, 115.74 (d, J=21.3 Hz), 128.44 (d, J=19.0 Hz), 128.77, 131.02, 131.10, 131.43, 136.19, 156.05, 162.26 (d, J=244 Hz), 176.15.

(R)-Methyl-(N-Benzyloxycarbonyl)-p-fluorophenylalaninate (3b)

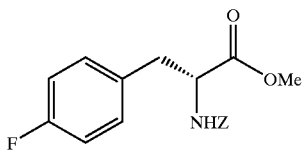

This product was obtained as a white solid in 48% isolated yield and 92% ee as determined by chiral HPLC analysis [Daicel chiralpak OD column, Hexanes:IPA, 95:5, 1.0 mL/min, λ 220 nm, t(major)=29.19 min, t(minor)=22.49 min]. $[\alpha]_D$=−(c 1.21, $CHCl_3$); $^1$H NMR (400 MHz, $CDCl_3$, 7.4:1 mixture of rotamers) δ 3.00–3.16 (m, 2H), 3.72 (s, 3H), 4.60–4.68 (m, 1H), 5.07 (d, J=12.0 Hz, 1H), 5.11 (d, J=12.0 Hz, 1H), 5.21–5.28 (m, 1H), 6.91–7.00 (m, 2H), 7.00–7.08 (m, 2H), 7.29–7.40 (m, 5H); $^1$H NMR (minor rotamer, partial) δ 2.90–3.02 (m, 2H), 3.64–3.72 (m, 3H), 4.46–4.55 (m, 1H); $^{13}$C NMR (100 MHz, $CDCl_3$) δ 37.66, 52.58, 55.01, 67.21, 115.65 (d, J=21.0 Hz), 128.38 (d, J=12.9 Hz), 128.74, 130.93, 131.01, 131.65, 136.39, 155.76, 162.22 (d, J=244 Hz), 172.00.

Ethyl (N-Benzyloxycarbonyl)-p-fluorophenylalaninate (5b)

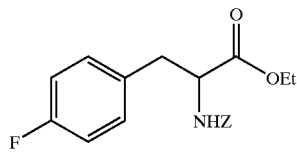

$^1$H NMR (400 MHz, $CDC_3$, 5.7:1 mixture of rotamers) δ 1.23 (t, J=7.0 Hz, 3H), 3.00–3.15 (m, 2H), 4.08–4.21 (m, 2H), 4.57–4.65 (m, 1H), 5.07 (d, J=12.0 Hz, 1H), 5.12 (d, J=12.0 Hz, 1H), 5.25–5.34 (m, 1H), 6.91–7.00 (m, 2H), 7.00–7.08 (m, 2H), 7.29–7.40 (m, 5H); $^1$H NMR (minor rotamer, partial) δ 2.90–3.02 (m, 2H), 4.45–4.53 (m, 1H); $^{13}$C NMR (100 MHz, $CDCl_3$) δ 14.28, 37.70, 55.02, 61.75, 67.14, 115.55 (d, J=21.3 Hz), 128.35 (d, J=11.4 Hz), 128.71, 130.98, 131.06, 131.71, 136.41, 155.74, 162.18 (d, J=244 Hz), 171.52.

(S)-(N-Benzyloxycarbonyl)-p-chlorophenylalanine (4c)

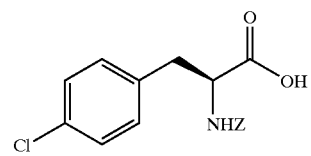

This product was obtained as a white solid in 43% isolated yield and 97% ee (as a ethyl ester) as determined by chiral HPLC analysis [Daicel chiralpak OJ column, Hexanes:IPA, 90:10, 1.0 mL/min, λ 220 nm, t(minor, ethyl ester)=21.10 min, t(major, ethyl ester)=24.92 min] from a reaction catalyzed by $(DHQD)_2AQN$ (10 mol %). This reaction employed 0.55 eq. of methanol and was stirred at −60° C. for 18 h when the reaction conversion reached 53%. $[\alpha]_D$=+4.1 (c 0.92, EtOH); $^1$H NMR (400 MHz, acetone-d6) δ 3.01 (dd, J=14.0 and 9.7 Hz, 1H), 3.23 (dd, J=14.0 and 4.9 Hz, 1H), 4.44–4.54 (m, 1H), 5.00 (d, J=12.8 Hz, 1H), 5.04 (d, J=12.8 Hz, 1H), 5.58 (d, J=8.5 Hz, 1H), 7.24–7.40 (m, 9H); $^{13}$C NMR (100 MHz, acetone-d6) δ 37.42, 55.95, 66.62, 128.49, 128.57, 129.11, 131.89, 132.80, 137.35, 138.11, 156.81, 173.02; IR (KBr) γ 3324, 3036, 2936, 1714, 1691, 1534, 1490, 1456, 1420, 1263, 1057 $cm^{-1}$; HRMS (DCI) exact mass calcd for $(C_{17}H1_7ClNO_4+NH_4^+)$ requires m/z 334.0846, found m/z 334.0856.

(R)-Methyl-(N-Benzyloxycarbonyl)-p-chlorophenylalaninate (3c)

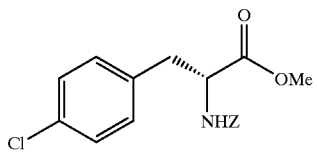

This product was obtained as a white solid in 52% isolated yield and 88% ee as determined by chiral HPLC analysis [Daicel chiralpak OJ column, Hexanes:IPA, 90:10, 1.0 mL/min, λ 220 nm, t(major)=31.25 min, t(minor)=37.17 min]. $[\alpha]_D$=−46.4 (c 1.21, $CHCl_3$); $^1$H NMR (400 MHz, $CDCl_3$, 8.5:1 mixture of rotamers) δ 3.03 (dd, 14.0 and 6.1 Hz, 1H), 3.12 (dd, J=14.0 and 5.5 Hz, 1H), 3.72 (s, 3H), 4.64 (m, 1H), 5.06 (d, J=12.2 Hz, 1H), 5.12 (d, J=12.2 Hz, 1H), 5.25 (d, J=7.9 Hz, 1H), 7.02 (d, J=8.5 Hz, 2H), 7.23 (d, J=8.5 Hz, 2H), 7.26–7.40 (m, 5H); $^1$H NMR (minor rotamer, partial) δ 2.88–2.98 (m, 2H), 3.67 (br s, 3H), 4.44–4.56 (m, 1H); $^{13}$C NMR (100 MHz, $CDCl_3$) δ 37.59, 52.39, 54.63, 67.00, 128.08, 128.23, 128.52, 128.70, 130.58, 133.02, 134.21, 136.13, 155.51, 171.67; IR ($CHCl_3$) γ 3345, 2956, 2930, 1731, 1715, 1520, 1494, 14371209, 1046 $cm^{-1}$; ; HRMS (DCI) exact mass calcd for $(C_{18}H_{19}ClNO_4+NH_4^+)$ requires m/z 348.1003, found m/z 348.1006.

Ethyl (N-Benzyloxycarbonyl)-p-chlorophenylalaninate (5c)

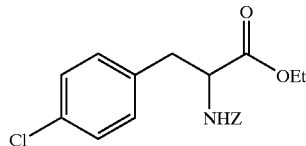

¹H NMR (400 MHz, CDCl₃, 6.2:1 mixture of rotamers) δ 1.23 (t, J=7.3 Hz, 3H), 3.03 (dd, J=13.7 and 6.1 Hz, 1H), 3.12 (dd, J=13.7 and 5.8 Hz, 1H), 4.16 (q, J=7.3 Hz, 2H), 4.56–4.66 (m, 1H), 5.07 (d, J=12.2 Hz, 1H), 5.12 (d, J=12.2 Hz, 1H), 5.28 (d, J=7.9 Hz, 1H), 7.03 (d, J=8.5 Hz, 2H), 7.18–7.40 (m, 7H); ¹H NMR (minor rotamer, partial) δ 2.88–2.98 (m, 2H), 4.42–4.52 (m, 1H); ¹³C NMR (100 MHz, CDCl₃) δ 14.08, 37.64, 54.65, 61.61, 66.96, 128.08, 128.21, 128.63, 130.66, 132.96, 134.29, 136.17, 155.51, 171.20.

(S)-(N-Benzyloxycarbonyl)-p-bromophenylalanine (4d)

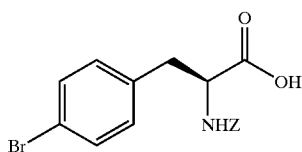

4d

This product was obtained as a white solid in 39% isolated yield and 97% ee (as a ethyl ester) as determined by chiral HPLC analysis [Daicel chiralpak OJ column, Hexanes:IPA, 80:20, 0.7 mL/min, λ 220 nm, t(minor, ethyl ester)=20.06 min, t(major, ethyl ester)=24.19 min] from a reaction catalyzed by (DHQD)₂AQN (10 mol %). This reaction employed 0.55 eq. of methanol and was stirred at −78° C. for 45 h when the reaction conversion reached 53%. [α]$_D$=+(c 0.92, EtOH); ¹H NMR (400 MHz, DMSO-d₆) δ 2.75–2.83 (m, 1H), 2.98–3.07 (m, 1H), 3.34 (s, br., 1H), 4.13–4.20 (m, 1H), 4.96 (s, 2H), 7.19–7.36 (m, 6H), 7.45 (d, J=8.0 Hz, 2H), 7.67 (d, J=8.8 Hz, 1H); ¹³C NMR (100 MHz, DMSO-d₆) δ 35.84, 55.24, 65.24, 119.59, 127.46, 127.71, 128.28, 131.00, 131.40, 136.99, 137.36, 155.97, 173.10.

(R)-Methyl-(N-Benzyloxycarbonyl)-p-chlorophenylaninate (3d)

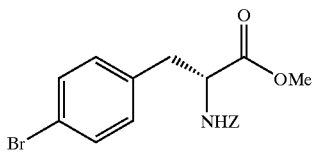

3d

This product was obtained as a white solid in 51% isolated yield and 87% ee as determined by chiral HPLC analysis [Daicel chiralpak OJ column, Hexanes:IPA, 80:20, 0.7 mL/min, λ 220 nm, t(major)=27.90 min, t(minor)=34.17 min]. [α]$_D$=−(c 1.21, CHCl₃); ¹H NMR (400 MHz, CDCl₃, 6.8:1 mixture of rotamers) δ 3.00 (dd, J=13.6 and 2.2 Hz, 1H), 3.11 (dd, J=13.6 and 1.2 Hz, 1H), 3.71 (s, 3H), 4.60–4.68 (m, 1H), 5.06 (d, J=12.0 Hz, 1H), 5.11 (d, J=12.0 Hz, 1H), 5.26–5.32 (m, 1H), 6.95 (d, J=8.0 Hz, 2H), 7.29–7.40 (m, 7H); ¹H NMR (minor rotamer, partial) δ 2.91–3.00 (m, 2H), 3.64–3.72 (m, 3H), 4.46–4.55 (m, 1H); ¹³C NMR (100 MHz, CDCl₃) δ 37.83, 52.61, 54.78, 67.20, 121.31, 128.28, 128.42, 128.72, 131.15, 131.85, 134.94, 136.33, 155.72, 171.86.

Ethyl (N-Benzyloxycarbonyl)-p-chlorophenylalaninate (5d)

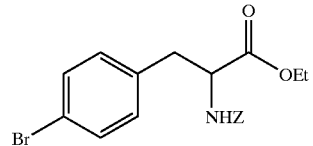

¹H NMR (400 MHz, CDCl₃, 5.5:1 mixture of rotamers) δ 1.23 (t, J=7.0 Hz, 3H), 3.01 (dd, J=14.0 and 2.2 Hz, 1H), 3.10 (dd, J=14.0 and 1.8 Hz, 1H), 4.16 (q, J=7.2 Hz, 2H), 4.58–4.66 (m, 1H), 5.06 (d, J=12.0 Hz, 1H), 5.11 (d, J=12.0 Hz, 1H), 5.25–5.31 (m, 1H), 6.97 (d, J=7.6 Hz, 2H), 7.30–7.42 (m, 7H); ¹H NMR (minor rotamer, partial) δ 2.88–2.96 (m, 2H), 4.45–4.52 (m, 1H); ¹³C NMR (100 MHz, CDCl₃) δ 14.31, 37.92, 54.81, 61.84, 67.18, 121.28, 128.30, 128.43, 128.73, 131.24, 131.80, 135.04, 136.38, 155.72, 171.40; IR (CHCl₃) γ 3338, 1732, 1715, 1592, 1515, 1455 cm⁻¹; HRMS (DCI) exact mass calcd for (C₁₉H₂₀NO₄Br+NH₄⁺) requires m/z 406.0654, found m/z 406.0653.

(S)-(N-Benzyloxycarbonyl)-3-(2-thienyl)alanine (4e)

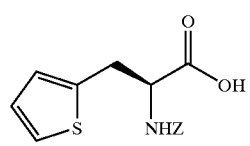

4e

This product was obtained as a white solid in 45% isolated yield and 94% ee (as an ethyl ester) as determined by chiral HPLC analysis [Daicel chiralpak OD column, Hexanes:IPA, 92.3:7.7, 0.8 mL/min, λ 220 nm, t(minor, ethyl ester)=23.12 min, t(major, ethyl ester)=16.42 min] from a reaction catalyzed by (DHQD)₂AQN (10 mol %). This reaction employed 0.55 eq. of methanol and was stirred at −78° C. for 25 h when the reaction conversion reached 50%. [α]$_D$=+48 (c 0.85, CHCl₃); Lit. (S, 99.8% ee) [α]$_D$=+54 (c 1.00, CHCl₃); ¹H NMR (400 MHz, CDCl₃, 7.1:1 mixture of rotamers) δ 3.35–3.42 (m, 2H), 4.68–4.72 (m, 1H), 5.11 (m, 2H), 5.44–5.48 (m, 1H), 6.79–6.81 (m, 1H), 6.85–6.91 (m, 1H), 7.10–7.15 (m, 1H), 7.29–7.37 (m, 5H), 10.69 (s, br., 1H); ¹H NMR (minor rotamer, partial) δ 3.18–3.26 (m, 1H), 3.30–3.38 (m, 1H), 4.47–4.55 (m, 1H), 6.38–6.44 (m, 1H); ¹³C NMR (100 MHz, CDCl₃) δ 32.16, 54.66, 67.45, 125.19, 127.14, 127.26, 128.28, 128.43, 128.71, 136.99, 156.09, 175.84.

(R)-Methyl-(N-Benzyloxycarbonyl)-3-(2-thienyl)alaninate (3e)

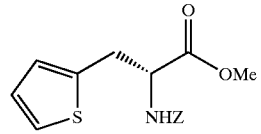

3e

This product was obtained as a colorless oil in 49% isolated yield and 94% ee as determined by chiral HPLC analysis [Daicel chiralpak OJ column, Hexanes:IPA, 90:10, 1.0 mL/min, λ 220 nm, t(major)=25.94 min, t(minor)=20.23 min]. [α]$_D$=−49 (c 1.30, CHCl₃); Lit. (S, 96.5% ee) [α]$_D$=+46 (c 1.00, CHCl₃); ¹H NMR (400 MHz, CDCl₃, 6.1:1 mixture of rotamers) δ 3.35–3.37 (m, 2H), 3.74 (s, 3H), 4.64–4.68 (m, 1H), 5.11 (s, 2H), 5.41–5.45 (m, 1H), 6.76–6.79(m, 1H), 6.89–6.93 (m, 1H), 7.14–7.16 (m, 1H), 7.30–7.39 (m, 5H); $^1$H NMR (minor rotamer, partial) δ 3.25–3.33 (m, 2H), 3.70 (s, 3H), 4.46–4.56 (m, 1H); $^{13}$C NMR (100 MHz, CDCl$_3$) δ 32.48, 52.66, 54.82, 67.17, 125.07, 126.98, 127.19, 128.22, 128.34, 128.68, 136.36, 137.23, 155.78, 171.50.

Ethyl (N-Benzyloxycarbonyl) 3-(2-thienyl)alaninate (5e)

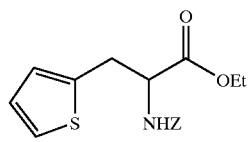

$^1$H NMR (400 MHz, CDC$_3$, 7.3:1 mixture of rotamers) δ 1.26 (t, J 7.0 Hz, 3H), 3.36–3.38 (m, 2H), 4.19 (q, J=7.0 Hz, 2H), 4.61–4.65 (m, 1H), 5.12 (s, 2H), 5.40–5.44 (m, 1H), 6.76–6.78 (m, 1H), 6.89–6.92 (m, 1H), 7.14–7.16 (m, 1H), 7.31–7.38 (m, 5H); $^1$H NMR (minor rotamer, partial) δ 3.26–3.32 (m, 2H), 4.48–4.56 (m, 1H); $^{13}$C NMR (100 MHz, CDCl$_3$) δ 14.28, 32.53, 54.82, 61.91, 67.16, 125.02, 127.02, 127.14, 128.24, 128.34, 128.69, 136.43, 137.32, 155.79, 171.03; IR (CHCl$_3$) γ 3343, 1732, 1715, 1586, 1514, 1457 cm$^{-1}$; HRMS (DCI) exact mass calcd for (C$_{17}$H$_{19}$NO$_4$S+H$^+$) requires m/z 334.1113, found m/z 334.1123

(N-Benzyloxycarbonyl)-2-aminocaprylic Acid (4f)

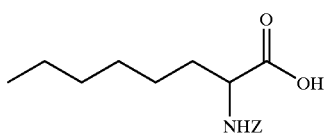

4f

This product was obtained as a colorless oil in 42% isolated yield and 94% ee (as a ethyl ester) as determined by chiral HPLC analysis [Daicel chiralpak OD column, Hexanes:IPA, 98.4:1.6, 1.0 mL/min, λ 220 nm, t(major, ethyl ester)=18.28 min, t(minor, ethyl ester)=28.54 min] from a reaction catalyzed by (DHQD)$_2$AQN (10 mol %). This reaction employed 0.56 eq. of methanol and was stirred at –60° C. for 37 h when the reaction conversion reached 49%. [α]$_D$=+4.1 (c 0.80, CHCl$_3$) $^1$H NMR (400 MHz, CDCl$_3$, 3.4:1 mixture of rotamers) δ 0.87 (t, J=6.7 Hz, 3H), 1.14–1.44 (m, 8H), 1.62–1.76 (m, 1H), 1.76–1.96 (m, 1H), 4.35–4.45 (m, 1H), 5.06–5.20 (m, 2H), 5.27 (d, J=7.9 Hz, 1H), 7.28–7.42 (m, 5H); $^1$H NMR (minor rotamer, partial) δ 4.20–4.30 (m, 1H), 6.20–6.30 (m, 1H); $^{13}$C NMR (100 MHz, CDCl$_3$, major rotamer) δ 14.00, 22.49, 25.08, 28.77, 31.50, 32.35, 53.73, 67.12, 128.11, 128.23, 128.53, 136.08, 156.02, 177.70; $^{13}$C NMR (minor rotamer, partial) δ 54.27, 67.54.

Methyl (N-Benzyloxycarbonyl)-2-aminocaprylate (3f)

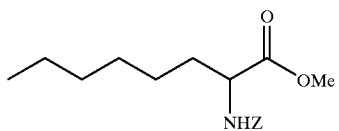

3f

This product was obtained as a light yellow oil in 49% isolated yield and 91% ee as determined by chiral HPLC analysis [Daicel chiralpak OD column, Hexanes:IPA, 98.4:1.6, 1.0 mL/min, λ220 nm, t(minor)=22.56 min, t(major)=32.41 min]. [α]$_D$=–7.9 (c 1.04, CHCl$_3$); $^1$H NMR (400 MHz, CDC$_3$, 6.1:1 mixture of rotamers) δ 0.87(t, J=6.7 Hz, 3H), 1.18–1.40 (m, 8H), 1.56–1.74 (m, 1H), 1.74–1.88 (m, 1H), 3.74 (s, 3H), 4.37 (dd, J=12.9 and 7.9 Hz, 1H), 5.11 (s, 2H), 5.29 (d, J=7.9 Hz, 1H), 7.28–7.42 (m, 5H); $^1$H NMR (minor rotamer, partial) δ 3.67 (s, 3H), 4.18–4.30 (m, 1H), 4.98–5.06 (m, 2H); $^{13}$C NMR (100 MHz, CDCl$_3$) δ 13.97, 24.46, 25.06, 28.76, 31.50, 32.63, 52.24, 53.84, 66.92, 128.07, 128.12, 128.48, 136.26, 155.83, 173.10.

Ethyl (N-Benzyloxycarbonyl)-2-aminocaprylate (5f)

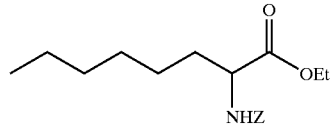

$^1$H NMR (400 MHz, CDCl$_3$, 13:1 mixture of rotamers) δ 0.87 (t, J=6.7 Hz, 3H), 1.14–1.44 (m, 1H), 1.56–1.72 (m, 1H), 4.19 (q, J=6.7 Hz, 2H), 4.35 (dd, J=12.9 and 7.9 Hz, 1H), 5.11 (s, 2H), 5.28 (d, J=7.9 Hz, 1H), 7.27–7.42 (m, 5H); $^1$H NMR (minor rotamer, partial) δ 4.96–5.06 (m, 2H); $^{13}$C NMR (100 MHz, CDCl$_3$) δ 13.98, 14.14, 22.47, 25.01, 28.79, 31.52, 32.69, 53.90, 61.30, 66.89, 128.07, 128.12, 128.49, 136.30, 155.82, 172.61; IR (CHCl$_3$) γ 3346, 2929, 2859, 1732, 1714, 1520, 1455, 1343, 1211, 1046 cm$^{-1}$; HRMS (DCI) exact mass calcd for (C$_{18}$H$_{27}$NO$_4$+NH$_4^+$) requires m/z 322.2018, found m/z 322.2016.

(S)-(N-Benzyloxycarbonyl)p-chlorophenylalanine (4g)

4g

This product was obtained as a colorless oil in 44% isolated yield and 91% ee (as an ethyl ester) as determined by chiral HPLC analysis [Daicel chiralpak OD+OJ column, Hexanes:IPA, 80:20, 0.6 mL/min, λ 220 nm, t(minor, ethyl ester)=50.43 min, t(major, ethyl ester)=44.19 min] from a reaction catalyzed by (DHQD)$_2$AQN (10 mol %). This reaction employed 0.55 eq. of methanol and was stirred at –78° C. for 72 h when the reaction conversion reached 51%. [α]$_D$=+18.1 (c 0.95, EtOH); Lit. (D) [α]$_D$=–17.0 (c 0.35, EtOH); $^1$H NMR (400 MHz, CDC$_3$, 6.5:1 mixture of rotamers) δ 3.68–3.74 (m, 1H), 3.91–3.97 (m, 1H), 4.52 (s, 2H), 4.52–4.57 (m, 1H), 5.08–5.16 (m, 2H), 5.66–5.71 (m, 1H), 7.24–7.39 (m, 1OH), 10.10 (s, br., 1H); $^1$H NMR (minor rotamer, partial) δ 3.81–3.89 (m, 1H), 4.38–4.43 (m, 1H), 6.11–6.17 (m, 1H); $^{13}$C NMR (100 MHz, CDCl$_3$) δ 54.37, 67.42, 69.67, 73.66, 127.90, 128.14, 128.31, 128.43, 128.68, 128.74, 136.26, 137.33, 156.37, 175.43.

(R)-Methyl-(N-Benzyloxycarbonyl)p-chlorophenylalanine (3g)

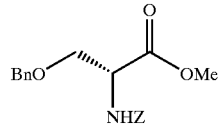

3g

This product was obtained as a white solid in 49% isolated yield and 89% ee as determined by chiral HPLC analysis [Daicel chiralpak OJ column, Hexanes:IPA, 85:15, 1.0 mL/min, λ 220 nm, t(major)=33.32 min, t(minor)=38.49 min]. [α]$_D$=–9.0 (c 1.45, CHCl$_3$); $^1$H NMR (400 MHz, CDCl$_3$) δ 3.68–3.72 (m, 1H), 3.75 (s, 3H), 3.87–3.91(m, 1H), 4.47 (d, J=12.0 Hz, 1H), 4.48–4.52 (m, 1H), 4.54 (d, J=12.0 Hz, 1H), 5.12 (s, 2H), 5.63–5.67(m, 1H), 7.23–7.39 (m, 10H); $^{13}$C NMR (100 MHz, CDCl$_3$) δ 52.75, 54.60, 67.23, 69.93, 73.47, 127.80, 128.06, 128.28, 128.37, 128.63, 128.72, 136.43, 137.63, 156.19, 170.99; IR (CHCl$_3$) γ 3344, 1732, 1715, 1586, 1515, 1454 cm$^{-1}$; HRMS (DCI) exact mass calcd for (C$_{17}$H$_{19}$NO$_4$S+H$^+$) requires m/z 344.1498, found m/z 344.1505.

Ethyl (N-Benzyloxycarbonyl)p-chlorophenylalanine (5g)

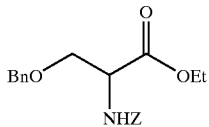

$^1$H NMR (400 MHz, CDCl$_3$) δ 1.24 (t, J=7.0 Hz, 3H), 3.70 (dd, J=9.2 and 2.8 Hz, 1H), 3.89 (dd, J=8.8 and 2.8 Hz, 1H), 4.20 (q, J=7.0 Hz, 2H), 4.45–4.56 (m, 2H), 4.48–4.52 (m, 1H), 5.12 (s, 2H), 5.64–5.68 (m, 1H), 7.23–7.38 (m, 10H); $^{13}$C NMR (100 MHz, CDCl$_3$) δ 14.31, 54.64, 61.84, 67.17, 70.02, 73.45, 127.78, 128.02, 128.26, 128.34, 128.60, 128.71, 136.48, 137.67, 156.19, 170.46.

(S)-(N-Benzyloxycarbonyl)valine (4h)

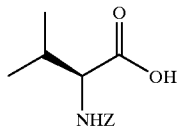

4h

This product was obtained as a white solid in 40% isolated yield and 96% ee (as a ethyl ester) as determined by chiral HPLC analysis [Daicel chiralpak AS and OJ column, Hexanes:IPA, 90:10, 0.8 mL/min, λ 220 nm, t(major, ethyl ester)=17.26 min, t(minor, ethyl ester)=19.49 min] from a reaction catalyzed by DHQD-PHN (20 mol %). This reaction employed 0.8 eq. of methanol and was stirred at 0° C. for 22h when the reaction conversion reached 59%. [α]$_D$=–0.62 (c 1.43, EtOH); (Literature, [α]D$^{25}$=+1.5 (c 5.0, EtOH), for S-enantiomer); $^1$H NMR (400 MHz, CDCl$_3$, 4:1 mixture of rotamers) δ 0.93 (d, J=6.7 Hz, 3H), 1.01 (d, J=6.7 Hz, 3H), 2.12–2.32 (m, 1H), 4.36 (dd, J=8.5 and 4.3 Hz, 1H), 5.12 (s, 2H), 5.29 (br d, J=8.5 Hz, 1H), 7.26–7.42 (m, 5H), 9.20–10.20 (br, 1H); $^1$H NMR (minor rotamer, partial) δ 4.14–4.24 (m, 1H), 5.15 (s, 2H), 6.18 (br d, J=8.5 Hz, 1H); $^{13}$C NMR (100 MHz, CDCl$_3$) δ 17.31, 18.99, 31.00, 58.81, 67.20, 128.14, 128.24, 128.54, 136.08, 156.35, 177.05.

Methyl (R)-N-Benzyloxycarbonyl)valinate (3h)

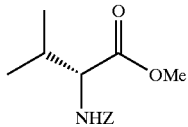

3h

This product was obtained as a white solid in 58% isolated yield and 67% ee as determined by chiral HPLC analysis [Daicel chiralpak AS and OJ column, 9:1, Hexanes:IPA, 0.8 mL/min, λ 220 nm, t(minor)=24.08 min, t(major)=25.92 min]. [α]$_D$=+11.1 (c 1.40, MeOH); (Literature, [α]$_D^{20}$=18.9 (c 1.0, MeOH), for S-enantiomer); $^1$H NMR (400 MHz, CDCl$_3$, 7:1 mixture of rotamers) δ 0.96 (d, J=7.3 Hz, 3H), 2.06–2.20 (m, 1H), 3.73 (s, 3H), 4.31 (dd, J=8.5 and 4.9 Hz, 1H), 5.11 (s, 2H), 5.32 (br dd, J=8.5 Hz, 1H), 7.28–7.40 (m, 5H); $^1$H NMR (minor rotamer, partial) δ 3.68(s, 3H), 4.10–4.20 (m, 1H); $^{13}$C NMR (100 MHz, CDCl$_3$) δ 17.48, 18.87, 31.23, 52.06, 58.97, 66.97, 128.07, 128.12, 128.47, 136.21, 156.17, 172.49.

Ethyl (N-Benzyloxycarbonyl)valinate (5h)

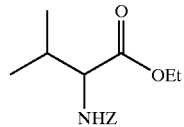

$^1$H NMR (400 MHz, CDCl$_3$) δ 0.89 (d, J=7.3 Hz, 3H), 0.97 (d, J=6.7 Hz, 3H), 1.28 (t, J=7.3 Hz, 3H), 2.04–2.22 (m, 1H), 4.21 (q, 7.3 Hz, 2H), 4.29 (dd, J=8.5 and 4.3 Hz, 1H), 5.11 (s, 3H), 5.31 (br d, J=8.5 Hz, 1H), 7.28–7.42 (m, 5H); $^{13}$C NMR (100 MHz, CDCl$_3$) δ 14.16, 17.43, 18.88, 31.29, 58.95, 61.18, 66.94, 128.08, 128.12, 128.48, 136.26, 156.18, 171.97.

(S)-(N-Benzyloxycarbonyl)phenylglycine (4i)

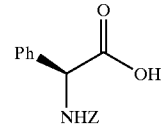

4i

This product was obtained as a white solid in 46% isolated yield and 84% ee (as a methyl ester) as determined by chiral HPLC analysis [Regis (R,R)Whelk-O 1 Reversible Column, Hexanes:IPA, 90:10, 1.0 mL/min, λ220 nm, t(minor, methyl ester)=16.69 min, t(major, methyl ester)=24.76 min] from a reaction catalyzed by (DHQD)$_2$AQN (10 mol %). This reaction employed 0.55 eq. of ethanol and was stirred at –78° C. for 16 h when the reaction conversion reached 46%. [α]$_D$=+95.6 (c 0.79, 95%EtOH); (Literature, [α]$_D^{25}$=+116.4 (c 1.0, 95% EtOH), for S-enantiomer); $^1$H NMR (400 MHz, CDCl$_3$) δ 5.06 (s, 2H), 5.18 (d, J=8.5 Hz, 1H), 7.24–7.44 (m, 10H), 8.15 (d, J=8.5 Hz, 1H); $^{13}$C NMR (100 MHz DMSO-d6) δ 58.05, 65.60, 127.75, 127.84, 127.93, 128.35, 128.43 (two carbons on the aromatic ring were overlapped), 136.92, 137.10, 155.87, 172.08.

(R)-Ethyl-(N-Benzyloxycarbonyl)pheylglycinate (3i)

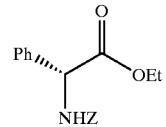

3i

This product was obtained as a white solid in 45% isolated yield and 97% ee as determined by chiral HPLC analysis [Regis (R, R) Whelk-O 1 Reversible Column, Hexanes:IPA, 90:10, 1.0 mL/min, λ 220 nm, t(major)=14.04 min, t(minor)=22.80 min]. [α]$_D$=–93.1 (c 0.95, CHCl$_3$); $^1$H NMR (400 MHz, CDCl$_3$15:1 mixture of rotamers) δ 1.20 (t, J=7.3 Hz, 3H), 4.04–4.24 (m, 2H), 5.06 (d, J=12.2 Hz, 1H), 5.12 (d, J=12.2 Hz, 1H), 5.36 (d, J=7.3 Hz, 1H), 5.87 (d, J=7.3 Hz, 1H), 7.25–7.44 (m, 10H); $^1$H NMR (minor rotamer, partial) δ 5.18–5.30 (m, 1H), 5.68–5.76 (m, 1H), 7.08–7.20 (m, 2H); $^{13}$C NMR (100 MHz, CDCl$_3$) δ 13.96, 57.97, 61.91, 67.08, 127.07, 128.15 (br, 2Cs), 128.88, 136.14, 136.77, 155.32, 170.76.

Methyl (N-Benzyloxycarbonyl) pheylglycinate

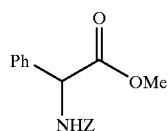

¹H NMR (400 MHz, CDCl₃, 5:1 mixture of rotamers) δ 3.72 (s, 3H), 5.07 (d, J=8.2 Hz, 1H), 5.12 (d, J=8.2 Hz, 1H), 5.38 (d, J=7.3 Hz, 1H), 5.85 (d, J=7.3 Hz, 1H), 7.25–7.38 (m, 10H); ¹H NMR (minor rotamer, partial) δ 3.66 (s, 3H), 5.20–5.28 (m, 1H), 5.64–5.74 (m, 1H), 7.06–7.18 (m, 2H); ¹³C NMR (100 MHz, CDCl₃) δ 52.79, 57.90, 67.11, 121.12, 128.15, 128.19, 128.51, 128.58, 128.95, 136.10, 136.57, 155.31, 171.26.

(S)-(N-Benzyloxycarbonyl)-p-chlorophenylalanine (4j)

This product was obtained as a white solid in 41% isolated yield and 95% ee (as an ethyl ester) as determined by chiral HPLC analysis [Daicel chiralpak OD+Hypersil column, Hexanes:IPA, 96.8:3.2, 1.0 mL/min, λ 220 nm, t(minor, methyl ester)=52.49 min, t(major, methyl ester)=61.61 min] from a reaction catalyzed by (DHQD)₂AQN (10 mol %). This reaction employed 0.55 eq. of ethanol and was stirred at −78° C. for 85 h when the reaction was quenched at the conversion of 56%. [α]$_D$=+105 (c 1.14, CHCl₃); ¹H NMR (400 MHz, CDCl₃, 1.9:1 mixture of rotamers) δ 3.71(s, 3H), 5.03 (s, 2H), 5.28–5.33 (m, 1H), 5.97–6.02 (m, 1H), 6.79–6.85 (m, 2H), 7.17–7.33 (m, 7H), 8.76 (s, br., 1H); ¹H NMR (minor rotamer, partial) δ 3.75 (s, 3H), 4.93–5.08 (m, 2H), 5.15–5.20 (m, 1H), 6.97–7.04 (m, 2H), 7.59–7.64 (m, 1H); ¹³C NMR (100 MHz, CDCl₃) δ 55.36, 57.38, 67.35, 114.46, 127.74, 128.24, 128.31, 128.37, 128.62, 136.07, 155.80, 159.85, 174.73; 13C NMR (minor rotamer, partial) δ 57.95, 67.67, 114.29, 129.27, 135.07, 156.92, 159.73, 173.92; IR (CHCl₃) γ 3348, 1732, 1715, 1611, 1586, 1513, 1455 cm⁻¹; HRMS (DCI) exact mass calcd for (C₁₇H₁₇NO₅+H⁺) requires m/z 316.1185, found m/z 316.1173.

(R)-Methyl-(N-Benzyloxycarbonyl)p-chlorophenylalanine (3j)

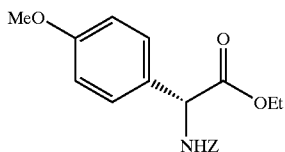

This product was obtained as a colorless oil in 55% isolated yield and 74% ee as determined by chiral HPLC analysis [Daicel chiralpak OD+Hypersil column, Hexanes:IPA, 96.8:3.2, 1.0 mL/min, λ 220 nm, t(major)= 43.45 min, t(minor)=48.95 min]. [α]$_D$=−68 (c 1.61, CHCl₃); ¹H NMR (400 MHz, CDCl₃, 7.5:1 mixture of rotamers) δ 1.19 (t, J=7.4 Hz, 3H), 3.77 (s, 3H), 4.08–4.23 (m, 2H), 5.06 (d, J=12.4 Hz, 1H), 5.11 (d, J=12.4 Hz, 1H), 5.28–5.31 (m, 1H), 5.87–5.90 (m, 1H), 6.86 (d, J=8.4 Hz, 2H), 7.24–7.36 (m, 7H); ¹H NMR (minor rotamer, partial) δ 5.13–5.18 (m, 1H), 5.57–5.63 (m, 1H), 7.13–7.19 (m, 1H); ¹³C NMR (100 MHz, CDCl₃) δ 14.11, 55.37, 57.54, 61.92, 67.12, 114.38, 128.28, 128.50, 128.62, 128.97, 136.33, 155.49, 159.79, 171.16; IR (CHCl₃) γ 3354, 1732, 1715, 1612, 1587, 1514, 1455 cm⁻¹; HRMS (DCI) exact mass calcd for (C₁₉H₂NO₅+H⁺) requires m/z 344.1498, found m/z 344.1501.

Ethyl (N-Benzyloxycarbonyl)p-chlorophenylalanine (5j)

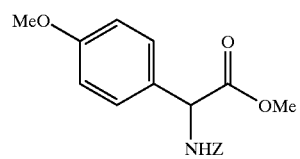

¹H NMR (400 MHz, CDC₃, 6.8:1 mixture of rotamers) δ 3.69 (s, 3H), 3.76 (s, 3H), 5.04 (d, J=12.2 Hz, 1H), 5.10 (d, J=12.2 Hz, 1H), 5.29–5.34 (m, 1H), 5.88–5.91 (m, 1H), 6.86 (d, J=8.4 Hz, 2H), 7.24–7.36 (m, 7H); ¹H NMR (minor rotamer, partial) δ 3.60–3.66 (m, 3H), 5.14–5.20 (m, 1H), 5.68–5.74 (m, 1H), 7.13–7.19 (m, 1H); ¹³C NMR (100 MHz, CDCl₃) δ 52.84, 55.38, 57.47, 67.16, 114.45, 128.28, 128.55, 128.62, 128.76, 136.29, 155.49, 159.87, 171.68; IR (CHCl₃) γ 3357, 1732, 1714, 1613, 1586, 1514, 1452 cm⁻¹; HRMS (DCI) exact mass calcd for (C₈H₁₉NO₅+H⁺) requires m/z 330.1341, found m/z 330.1331.

(S)-N-(9-Fluorenylmethoxycarbonyl)phenylalanine (4k)

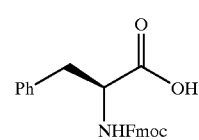

This product was obtained as a white solid in 47% isolated yield and 96% ee (as a ethyl ester) as determined by chiral HPLC analysis [Daicel chiralpak OD column, Hexanes:IPA, 80:20, 1.0 mL/min, λ 254 nm, t(major, ethyl ester)=27.48 min, t(minor, ethyl ester)=17.22 min] from a reaction catalyzed by (DHQD)₂AQN (10 mol %). This reaction employed 0.55 eq. of methanol and was stirred at −78° C. for 46 h when the reaction conversion reached 51%. [α]$_D$=−35.2 (c 1.27, DMF); (Literature, [α]$_D^{20}$=37 (c 1.0, DMF), for S-enantiomer); ¹H NMR (400 MHz, acetone-d6, 6:1 mixture of rotamers) δ 3.04 (dd, J=14.0 and 9.5 Hz, 1H), 3.25 (dd, J=14.0 and 4.9 Hz, 1H), 4.15–4.24 (m, 1H), 4.24–4.34 (m, 1H), 4.49–4.57 (m, 1H), 6.72 (d, J=7.9 Hz, 1H), 7.19–7.26 (m, 1H), 7.26–7.36 (m, 5H), 7.36–7.44 (m, 2H), 7.58–7.70 (m, 2H), 7.85 (d, J=7.9 Hz, 2H); ¹H NMR (minor rotamer, partial) δ 2.86–2.96 (m, 1H), 3.10–3.18 (m, 1H), 4.40–4.49 (m, 1H), 6.08–6.18 (m, 1H); ¹³C NMR (100 MHz, acetone-d6) δ 38.13, 47.89, 56.16, 67.11, 120.72, 126.08, 126.14, 127.40, 127.87, 128.45, 129.13, 130.14, 138.40, 142.02, 144.94, 156.74, 173.29.

(R)-Methyl-N-(9-Fluorenylmethoxycarbonyl)phenylalaninate (3k)

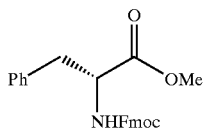

This product was obtained as a white solid in 50% isolated yield and 92% ee as determined by chiral HPLC analysis [Daicel chiralpak OJ column, Hexanes:IPA, 80:20, 1.0 mL/min, λ 254 nm, t(major)=24.91 min, t(minor)=19.70 min] [α]$_D$=−33.1 (c 1.50, CHCl$_3$); $^1$H NMR (400 MHz, CDCl$_3$, 6:1 mixture of rotamers) δ 3.08–3.20 (m, 2H), 3.72 (s, 3H), 4.12–4.24 (m, 1H), 4.28–4.38 (m, 1H), 4.38–4.54 (m, 1H), 4.67 (dd, J=14.0 and 6.1 Hz, 1H), 5.26 (d, J=8.5 Hz, 1H), 7.04–7.14 (m, 2H), 7.20–7.35 (m, 5H), 7.35–7.44 (m, 2H), 7.49–7.60 (m, 2H), 7.76 (d, J=7.3 Hz, 2H); $^1$H NMR (minor rotamer, partial) δ 2.82–2.90 (m, 2H), 3.66 (s, 3H), 4.02–4.08 (m, 1H), 4.88–4.98 (m, 1H), 6.95–7.02 (m, 2H); 13C NMR (100 MHz, CDCl$_3$) δ 38.19, 47.12, 52.34, 54.73, 66.90, 119.96, 125.02, 125.08, 127.03, 127.14, 127.69, 128.59, 129.27, 135.66, 141.28, 143.70, 155.50, 171.90.

Ethyl N-(9-Fluorenylmethoxycarbonyl)phenylalaninate (5k)

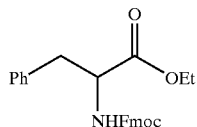

$^1$H NMR (400 MHz, CDCl$_3$, 5.6:1 mixture of rotamers) δ 1.25 (t, J=7.3 Hz, 3H), 3.05–3.18 (m, 2H), 4.08–4.26 (m, 3H), 4.30–4.40 (m, 1H), 4.40–4.52 (m, 1H), 5.28 (d, J=7.9 Hz, 1H), 7.06–7.16 (m, 2H), 7.22–7.37 (m, 5H), 7.37–7.46 (m, 2H), 7.50–7.62 (m, 2H), 7.77 (d, J=7.3 Hz, 2H); $^1$H NMR (minor rotamer, partial) δ 2.82–2.92 (m, 2H), 4.89–4.99 (m, 1H), 6.97–7.04 (m, 2H); $^{13}$C NMR (100 MHz, CDCl$_3$) δ 14.09, 38.29, 47.15, 54.76, 61.54, 66.90, 119.97, 125.05, 127.04, 127.70, 128.54, 129.37, 135.76, 141.29, 143.73, 155.51, 171.46.

(S)-(N-t-Butyloxycarbonyl)phenylalanine (41)

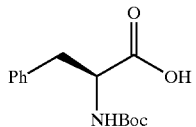

This product was obtained as a white solid in 41% isolated yield and 98% ee (as a ethyl ester) as determined by chiral HPLC analysis [Daicel chiralpak OD and OJ column, Hexanes:IPA, 99:1, 0.8 mL/min, λ 220 nm, t(minor, ethyl ester)=27.73 min, t(major, ethyl ester)=33.26 min] from a reaction catalyzed by (DHQD)$_2$AQN (20 mol %). This reaction employed 1.0 eq. of methanol and was stirred at −40° C. for 15 h when the reaction conversion reached 59%. The reaction was quenched with 5% HOAc (2 mL) and the organic layer was washed with 0.2 N HCl (2×1 mL), concentrated under reduced pressure, dissolved in a mixture of H$_2$O/THF (v/v: ¼) and stirred at room temperature overnight. The solvents were removed under vacuum and the residue was dissolved in ether (10 mL) and extracted with 1N Na$_2$CO$_3$ (3 mL). The organic layer was washed with saturated brine (1 mL), dried over anh. Na$_2$SO$_4$, filtered and concentrated under vacuum to give methyl ester as a white solid. The basic aq. phase was acidified with 0.5 N HCl till pH<4, then extracted with ethyl acetate (3×4 mL), the combined extract was dried over anh. Na$_2$SO$_4$, filtered and concentrated to give the acid as a white solid. [α]$_D$=−4.2 (c 0.91, AcOH); (Literature, [α]$_D$=−4.0 (c 4.0, AcOH), for S-enantiomer) $^1$H NMR (400 MHz, CDCl$_3$, 2:1 mixture of rotamers) δ 1.42 (s, 9H), 3.00–3.28 (m, 2H), 4.54–4.70 (m, 1H), 4.98 (d, J=6.7 Hz, 1H), 7.12–7.40 (m, 5H), 7.70–8.70 (br, 1H); $^1$H NMR (minor rotamer, partial) δ 1.30 (s, 9H), 2.84–3.00 (m, 1H), 4.34–4.50 (m, 1H), 6.30–6.42 (m, 1H); $^{13}$C NMR (100 MHz, CDCl$_3$, major rotamer) δ 28.26, 37.79, 54.28, 80.29, 127.07, 128.58, 129.37, 135.82, 155.37, 176.46; $^{13}$C NMR (minor rotamer, partial) δ 28.03, 39.06, 56.03, 81.52, 136.34, 156.24.

(R)-Methyl-(N-t-Butyloxycarbonyl)phenylalaninate (31)

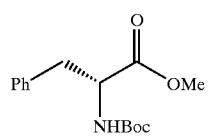

This product was obtained as a white solid in 56% isolated yield and 67% ee as determined by chiral HPLC analysis [Daicel chiralpak OD and OJ column, Hexanes:IPA, 99:1, 0.8 mL/min, λ 220 nm, t(major)=36.73 min, t(minor)=50.30 min]. [α]$_D$=−27.7 (c 1.11, CHCl$_3$); $^1$H NMR (400 MHz, CDCl$_3$, 5.4:1 mixture of rotamers) δ 1.42 (s, 9H), 3.00–3.18 (m, 2H), 3.72 (s, 3H), 4.59 (dd, J=14.0 and 6.1 Hz, 1H), 4.97 (d, J=7.3 Hz, 1H), 7.12 (d, J=7.3 Hz, 2H), 7.20–7.36 (m, 3H); $^1$H NMR (minor rotamer, partial) δ 2.88–3.00 (m, 2H), 4.36–4.46 (m, 1H), 4.64–4.74 (m, 1H); $^{13}$C NMR (100 MHz, CDCl$_3$) δ 28.22, 38.27, 52.10, 54.37, 79.82, 126.94, 128.47, 129.22, 135.97, 155.02, 172.29.

Ethyl (N-t-Butyloxycarbonyl)phenylalaninate (51)

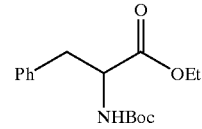

$^1$H NMR (400 MHz, CDCl$_3$ 5.6:1 mixture of rotamers) δ 1.23 (t, J=6.7 Hz, 3H), 1.42 (s, 9H), 3.00–3.16 (m, 2H), 4.16 (q, J=6.7 Hz, 2H), 4.56 (dd, J=13.4 and 6.1 Hz, 1H), 4.98 (d, J=7.3 Hz, 1H), 7.14 (d, J=7.3 Hz, 2H), 7.20–7.36 (m, 3H); $^1$H NMR (minor rotamer, partial) δ 2.88–3.00 (m, 2H), 4.30–4.44 (m, 1H), 4.64–4.76 (m, 1H); $^{13}$C NMR (100 MHz, CDCl$_3$) δ 14.08, 28.28, 38.39, 54.43, 61.29, 79.80, 126.94, 128.46, 129.34, 136.08, 155.07, 171.85.

(S)-(N-Allyloxycarbonyl)phenylalanine (4m)

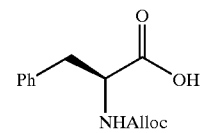

This product was obtained as a white solid in 45% isolated yield and 91% ee (as a ethyl ester) as determined by chiral HPLC analysis [Daicel chiralpak AS and OD column, Hexanes:IPA, 97:3, 1.0 mL/min, λ 220 nm, t(major, ethyl ester)=39.29 min, t(minor, ethyl ester)=45.34 min] from a reaction catalyzed by (DHQD)₂AQN (10 mol %). This reaction employed 0.55 eq. of methanol and was stirred at −60° C. for 15 h when the reaction conversion reached 51%. [α]_D=+9.5 (c 0.77, CHCl₃); (Literature, [α]_D=+35.8 (c 1.0, CHCl₃), for S-enantiomer) ¹H NMR (400 MHz, CDCl₃, 5:1 mixture of rotamers) δ 3.06–3.28 (m, 2H), 4.48–4.64 (m, 2H), 4.64–4.76 (m, 1H), 5.10–5.36 (m, 3H), 5.83–5.96 (m, 1H), 7.18 (d, J=7.3 Hz, 2H), 7.22–7.40 (m, 3H), 7.60–7.80 (br, 1H); ¹H NMR (minor rotamer, partial) δ 2.92–3.06 (m, 1H), 4.40–4.48 (m, 1H), 5.74–5.83 (m, 1H); ¹³C NMR (100 MHz, CDCl₃) δ 37.70, 54.48, 66.00, 117.99, 127.26, 128.69, 129.30, 132.39, 135.43, 155.74, 176.39; ¹³C NMR (minor rotamer, partial) δ 55.55, 66.40.

(R)-Methyl-(N-Allyloxycarbonyl)phenylalaninate (3m)

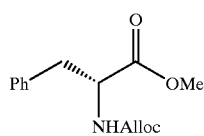

3m

This product was obtained as a colorless oil in 44% isolated yield and 91% ee as determined by chiral HPLC analysis [Daicel chiralpak OD column, Hexanes:IPA, 98.6:1.4, 1.0 mL/min, λ 220 nm, t(minor)=28.74 min, t(major)=36.38 min]. [α]_D=−43.6 (c 0.97, CHCl₃); (Literature, [α]_D=+43.3 (c 0.8, CHCl₃), for S-enantiomer) ¹H NMR (400 MHz, CDCl₃) δ 3.00–3.18 (m, 2H), 3.72 (s, 3H), 4.56 (d, J=5.5 Hz, 2H), 4.65 (dd, J=14.0 and 6.1 Hz, 1H), 5.14–5.34 (m, 3H), 5.80–5.96 (m, 1H), 7.12 (d, J=7.3 Hz, 2H), 7.20–7.36 (m, 3H); ¹³C NMR (100 MHz, CDCl₃) δ 38.21, 52.26, 54.70, 65.76, 117.75, 127.11, 128.58, 129.21, 132.56, 135.69, 155.47, 171.98.

Ethyl (N-Allyloxycarbonyl)phenylalaninate (5m)

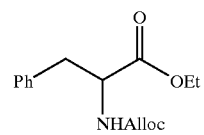

¹H NMR (400 MHz, CDCl₃) δ 1.23 (t, J=7.0 Hz, 3H), 3.00–3.18 (m, 2H), 4.17 (q, J=7.0 Hz, 2H), 4.56 (d, J=5.5 Hz, 2H), 4.63 (dd, J=13.6 and 6.3 Hz, 1H), 5.16–5.34 (m, 3H), 7.14 (d, J=7.8 Hz, 2H), 7.20–7.36 (m, 3H); ¹³C NMR (100 MHz, CDCl₃) δ 14.05, 38.29, 54.73, 61.42, 65.72, 117.73, 127.06, 128.52, 129.29, 132.61, 135.77, 155.46, 171.51.

(N-Allyloxycarbonyl)homophenylalanine (4n)

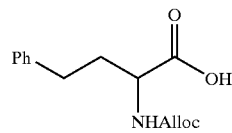

4n

This product was obtained as a colorless oil in 41% isolated yield and 96% ee as determined by chiral HPLC analysis [Daicel chiralpak OJ column, Hexanes:IPA:TFA, 96:4:0.1, 1.0 mL/min, λ 254 nm, t(minor) 23.55 min, t(major)=27.96 min] from a reaction catalyzed by (DHQD)₂AQN (10 mol %). This reaction employed 0.60 eq. of methanol and was stirred at −60° C. for 36 h when the reaction conversion reached 53%. [α]_D=+22.7 (c 0.67, CHCl₃); ¹H NMR (400 MHz, CDCl₃, 3:1 mixture of rotamers) δ 1.96–2.10 (m, 1H), 2.16–2.30 (m, 1H), 2.64–2.80 (m, 2H), 4.38–4.48 (m, 1H), 4.59 (d, J=5.5 Hz, 2H), 5.18–5.28 (m, 1H), 5.28–5.40 (m, 2H), 5.82–5.98 (m, 1H), 7.12–7.24 (m, 3H), 7.24–7.34 (m, 2H), 7.60–8.60 (br, 1H); ¹H NMR (minor rotamer, partial) δ 4.23–4.33 (m, 1H), 6.44–6.54 (m, 1H); ¹³C NMR (100 MHz, CDCl₃, major rotamer) δ 31.51, 33.95, 53.44, 66.05, 118.03, 126.25, 128.39, 128.52, 132.42, 140.36, 155.95, 176.97; ¹³C NMR (minor rotamer, partial) δ 53.64, 66.54; IR (CHCl₃) γ 3319, 3027, 2932, 1714, 1698, 1538, 1498, 1455, 1410, 1337 cm⁻¹.

Methyl (N-Allyloxycarbonyl)homophenylalaninate (3n)

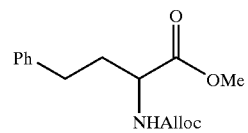

3n

This product was obtained as a colorless oil in 54% isolated yield and 81% ee as determined by chiral HPLC analysis [J. T. Baker DNBPG (ionic) +Regis (R,R)-Whelk-O1, Hexanes:IPA, 98:2, 0.75 mL/min, λ 220 nm, t(major)= 39.80 min, t(minor)=38.21 min]. [α]_D=−31.7 (c 0.97, CHCl₃); ¹H NMR (400 MHz, CDCl₃, 6.3:1 mixture of rotamers) δ 1.92–2.04 (m, 1H), 2.12–2.24 (m, 1H), 2.62–2.74 (m, 2H), 3.72 (s, 3H), 4.36–4.46 (m, 1H), 4.59 (d, J=5.5 Hz, 2H), 5.18–5.38 (m, 3H), 5.85–6.00 (m, 1H), 7.15–7.23 (m, 3H), 7.25–7.32 (m, 2H); ¹H NMR (minor rotamer, partial) δ 4.24–4.34 (m, 1H), 5.10–5.18 (m, 1H); ¹³C NMR (100 MHz, CDCl₃) δ 31.48, 34.21, 52.36, 53.53, 65.83, 117.83, 126.18, 128.36, 128.46, 132.57, 140.53, 155.72, 172.79; IR (neat) γ 3334, 3028, 2953, 1731, 1715, 1520, 1498, 1455, 1335 cm⁻¹.

Ethyl (N-Allyloxycarbonyl)homophenylalaninate (5n)

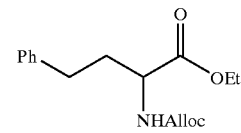

¹H NMR (400 MHz, CDCl₃, 6.8:1 mixture of rotamers) δ 1.28 (t, J=7.3 Hz, 3H), 1.92–2.04 (m, 1H), 2.12–2.24 (m, 1H), 2.60–2.75 (m, 2H), 4.18 (q, J=7.3 Hz, 2H), 4.35–4.45 (m, 1H), 4.59 (d, J=5.5 Hz, 2H), 5.18–5.26 (m, 1H), 5.26–5.40 (m, 2H), 5.85–5.98 (m, 1H), 7.13–7.24 (m, 3H), 7.24–7.32 (m, 2H); ¹H NMR (minor rotamer, partial) δ 4.23–4.33 (m, 1H), 5.10–5.18 (m, 1H); ¹³C NMR (100 MHz, CDCl₃) δ 14.14, 31.47, 34.34, 53.63, 61.47, 65.79, 117.79, 126.15, 128.36, 128.46, 132.60, 140.67, 155.72, 172.28; IR (neat) γ 3340, 3025, 2980, 1731, 1715, 1522, 1498, 1455, 1374 cm⁻¹.

EXAMPLE 10
General Procedure for the Dynamic Kinetic Resolution of UNCAs

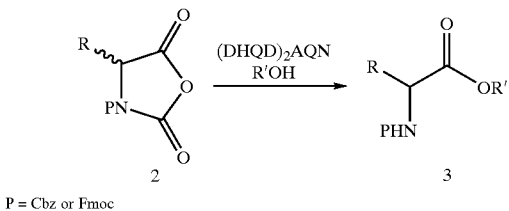

P = Cbz or Fmoc

Figure 7:
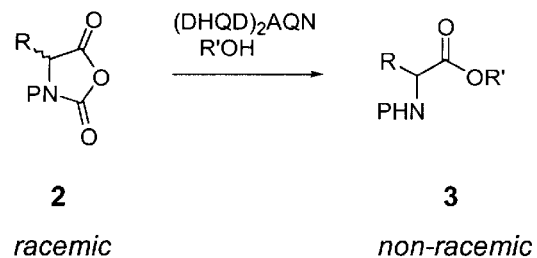
FIG. 7 tabulates the yields and enantiomeric excesses of the products of dynamic kinetic resolutions of various urethane-protected α-amino acid N-carboxy anhydrides.
Figure 8:
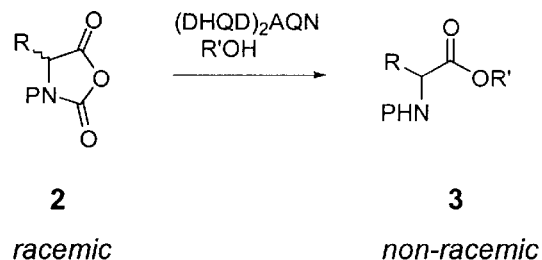
FIG. 8 tabulates the yields and enantiomeric excesses of the products of dynamic kinetic resolutions of various urethane-protected α-amino acid N-carboxy anhydrides.

A mixture of UNCA 2 (0.20 mmol) and 4A molecular sieves (20 mg) in anhydrous diethyl ether (14.0 mL) was stirred at room temperature for 10 minutes, then cooled to the temperature indicated in FIG. 7 or 8, after which the $(DHQD)_2AQN$ (0.040 mmol) was added to the mixture. The resulting mixture was stirred for 5 minutes, and then a solution of alcohol in ether (v/v=1/39, 0.12 mmol of alcohol) was introduced dropwise via a syringe over a period of 20 min. The resulting reaction mixture was stirred at the indicated temperature for 40 min. Another portion of a solution of alcohol in ether (v/v=1/39, 0.12 mmol of alcohol) was introduced dropwise via a syringe over a period of 20 min. After 40 min, aqueous HCl (2 N, 4.0 mL) was added to the reaction mixture, and the resulting mixture was stirred at room temperature for 10 min. The organic phase was collected, washed with aqueous HCl (2 N, 2×1 mL), dried over sodium sulfate, and concentrated to provide product 3, with or without further purification by flash chromatography (Ethyl acetate:Hexanes=1:9).

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are encompassed by the following claims.

We claim:

1. A method of kinetic resolution represented by Scheme 1:

Scheme 1

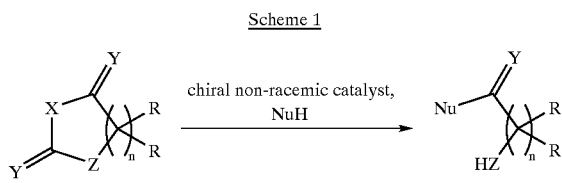

wherein

X represents NR', O, or S;

Y represents independently for each occurrence O or S;

Z represents NR', O, or S;

R represents independently for each occurrence hydrogen, or optionally substituted alkyl, aryl, heteroaryl, aralkyl, or heteroaralkyl;

R' represents independently for each occurrence R, formyl, acyl, sulfonyl, —$CO_2R$, or —$C(O)NR_2$;

the substrate and the product are chiral;

the substrate is racemic;

NuH represents water, an alcohol, a thiol, an amine, a β-keto ester, a malonate, or the conjugate base of any of them;

chiral non-racemic catalyst is a chiral non-racemic tertiary amine, phosphine, or arsine;

n is 1 or 2; and when said method is completed or interrupted, any unreacted substrate is racemic, and the enantiomeric excess of the product is greater than zero.

2. The method of claim 1, wherein X is O.

3. The method of claim 1, wherein Y is O.

4. The method of claim 1, wherein NuH represents an alcohol, a thiol, or an amine.

5. The method of claim 1, wherein NuH represents an alcohol.

6. The method of claim 1, wherein said chiral non-racemic catalyst is a chiral non-racemic tertiary amine.

7. The method of claim 1, wherein said chiral non-racemic catalyst is a cinchona alkaloid.

8. The method of claim 1, wherein said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

9. The method of claim 1, wherein X is O; and Y is O.

10. The method of claim 1, wherein X is O; Y is O; and NuH represents an alcohol, a thiol, or an amine.

11. The method of claim 1, wherein X is O; Y is O; and NuH represents an alcohol.

12. The method of claim 1, wherein X is O; Y is O; and said chiral non-racemic catalyst is a chiral non-racemic tertiary amine.

13. The method of claim 1, wherein X is O; Y is O; and said chiral non-racemic catalyst is a cinchona alkaloid.

14. The method of claim 1, wherein X is O; Y is O; and said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

15. The method of claim 1, wherein X is O; Y is O; NuH is an alcohol; and said chiral non-racemic catalyst is a tertiary amine.

16. The method of claim 1, wherein X is O; Y is O; NuH is an alcohol; and said chiral non-racemic catalyst is a cinchona alkaloid.

17. The method of claim 1, wherein X is O; Y is O; NuH is an alcohol; and said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

18. The method of claim 1, wherein the enantiomeric excess of the product is greater than about 50%.

19. The method of claim 1, wherein the enantiomeric excess of the product is greater than about 70%.

20. The method of claim 1, wherein the enantiomeric excess of the product is greater than about 90%.

21. A method of kinetic resolution represented by Scheme 2:

Scheme 2

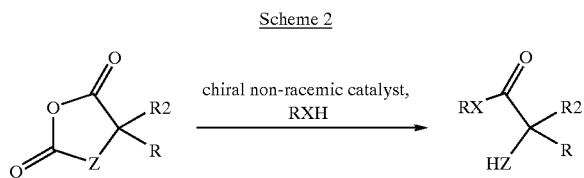

wherein
- X represents NR', O, or S;
- Z represents NR', O, or S;
- R and R2 represent independently for each occurrence hydrogen, or optionally substituted alkyl, aryl, heteroaryl, aralkyl, or heteroaralkyl; provided that R and R2 are not the same;
- R' represents independently for each occurrence R, formyl, acyl, sulfonyl, —$CO_2$R, or —C(O)$NR_2$;
- the substrate and the product are chiral;
- the substrate is racemic;
- chiral non-racemic catalyst is a chiral non-racemic tertiary amine, phosphine, or arsine; and
- when said method is completed or interrupted, any unreacted substrate is racemic, and the enantiomeric excess of the product is greater than zero.

22. The method of claim 21, wherein X represents O.

23. The method of claim 21, wherein Z represents NR' or O.

24. The method of claim 21, wherein said chiral non-racemic catalyst is a chiral non-racemic tertiary amine.

25. The method of claim 21, wherein said chiral non-racemic catalyst is a cinchona alkaloid.

26. The method of claim 21, wherein said chiral non-racemic catalyst is quinidine, $(DHQ)_2$PHAL, $(DHQD)_2$PHAL, $(DHQ)_2$PYR, $(DHQD)_2$PYR, $(DHQ)_2$AQN, $(DHQD)_2$AQN, DHQ-CLB, DHQD-CLB, DHQ-MEQ, DHQD-MEQ, DHQ-AQN, DHQD-AQN, DHQ-PHN, or DHQD-PHN.

27. The method of claim 21, wherein X represents O; and Z represents NR' or O.

28. The method of claim 21, wherein X represents O; Z represents NR' or O; and said chiral non-racemic catalyst is a chiral non-racemic tertiary amine.

29. The method of claim 21, wherein X represents O; Z represents NR' or O; and said chiral non-racemic catalyst is a cinchona alkaloid.

30. The method of claim 21, wherein X represents O; Z represents NR' or O; and said chiral non-racemic catalyst is quinidine, $(DHQ)_2$PHAL, $(DHQD)_2$PHAL, $(DHQ)_2$PYR, $(DHQD)_2$PYR, $(DHQ)_2$AQN, $(DHQD)_2$AQN, DHQ-CLB, DHQD-CLB, DHQ-MEQ, DHQD-MEQ, DHQ-AQN, DHQD-AQN, DHQ-PHN, or DHQD-PHN.

31. The method of claim 21, wherein the enantiomeric excess of the product is greater than about 50%.

32. The method of claim 21, wherein the enantiomeric excess of the product is greater than about 70%.

33. The method of claim 21, wherein the enantiomeric excess of the product is greater than about 90%.

* * * * *